United States Patent [19]

Talebian et al.

[11] Patent Number: 5,091,523
[45] Date of Patent: Feb. 25, 1992

[54] MITOMYCIN DERIVATIVES HAVING REDUCED BONE MARROW TOXICITY, PROCESSES FOR THEIR PREPARATION, AND THE USES THEREOF

[75] Inventors: Abdolhossen Talebian, Herndon; Dianna Green, Falls Church, both of Va.; Charles Hammer, Washington, D.C.; Philip Schein, Bryn Mawr, Pa.; Alem Ghiorghis, Washington, D.C.; Robert R. Clarke, Bethesda, Md.

[73] Assignee: Georgetown University, Washington, D.C.

[21] Appl. No.: 620,853

[22] Filed: Dec. 3, 1990

Related U.S. Application Data

[63] Continuation-in-part of Ser. No. 513,266, Apr. 25, 1990, abandoned, which is a continuation-in-part of Ser. No. 235,224, Aug. 23, 1988, abandoned.

[51] Int. Cl.$^5$ .................. A61K 31/40; A61K 21/00; C07D 487/14
[52] U.S. Cl. .................. 536/17.3; 536/17.4; 536/22; 536/43; 514/908; 548/422
[58] Field of Search .................. 536/22, 17.3, 17.4, 536/43; 548/422; 514/908

[56] References Cited

U.S. PATENT DOCUMENTS

| | | | |
|---|---|---|---|
| 3,226,393 | 12/1965 | Meyer et al. | 548/422 |
| 3,367,945 | 2/1968 | Matsui et al. | 548/422 |
| 3,450,705 | 6/1969 | Matsui et al. | 548/422 |
| 4,021,449 | 5/1977 | Fujimoto et al. | 548/422 |
| 4,268,676 | 5/1981 | Remers | 548/422 |
| 4,395,558 | 7/1983 | Kasai et al. | 548/422 |
| 4,720,543 | 1/1988 | McPherson et al. | 548/422 |
| 4,746,746 | 5/1988 | Remers | 548/422 |
| 4,771,068 | 9/1988 | Kasai et al. | 548/422 |
| 4,791,130 | 12/1988 | Kuroda et al. | 548/422 |
| 4,814,445 | 3/1989 | Vyas et al. | 548/422 |
| 4,820,824 | 4/1989 | Kono et al. | 548/422 |

FOREIGN PATENT DOCUMENTS 9001931 3/1990 PCT Int'l Appl.

OTHER PUBLICATIONS

Kinoshita, S. et al., *J. Med. Chem.* 14:103-112 (1971).
Anderson, T. et al., *Cancer Res.*, 35:761-765 (1975).
Iyengar, B. et al., *J. Med. Chem.*, 24:975-981 (1981).
Iyengar, B. et al., *J. Med. Chem.*, 26:16-20 (1983).
Iyengar, B. et al., *J. Med. Chem.*, 26:1453-1457 (1983).
Iyengar, B. et al., *J. Med. Chem.*, 29:1864-1868 (1986).
Matsui, M. et al., *Chem. Abstr.*, 69:8138 (Abstr. 86986k) (1968).
Oboshi, S., et al., *GANN*, 58:315-321 (1967).
Sami, S. M. et al., *J. Med. Chem.*, 27:701-708 (1984).
Schein, P. S. et al., *Cancer Res.*, 47:696-699 (1987).
Talebian et al., *Proc. AACR*, 28:Abstr. 1025 (1987).
Usubuchi, I., et al., *GANN*, 58:307-313 (1967).

*Primary Examiner*—Ronald W. Griffin
*Attorney, Agent, or Firm*—Sterne, Kessler, Goldstein & Fox

[57] ABSTRACT

The invention relates to certain derivatives of mitomycins A and C and the use thereof to treat bacterial infections and to supress the growth of cancer cells. The invention also relates to processes for the preparation of the mitomycin derivatives of the invention.

49 Claims, 5 Drawing Sheets

MITOMYCIN DERIVATIVES HAVING REDUCED BONE MARROW TOXICITY, PROCESSES FOR THEIR PREPARATION, AND THE USES THEREOF

CROSS REFERENCE TO RELATED APPLICATION

This application is a continuation-in-part of U.S. application Ser. No. 07/513,266, filed Apr. 25, 1990, now abandoned, which is a continuation-in-part of U.S. Ser. No. 07/235,224, filed Aug. 23, 1988, now abandoned, the disclosures of which are fully incorporated by reference herein.

FIELD OF THE INVENTION

The invention is in the field of pharmaceutical agents and the uses thereof.

BACKGROUND OF THE INVENTION

The mitomycins are a family of compounds having the following general Formula (I):

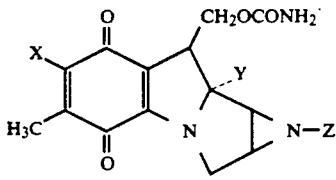

Mitomycins A, B and C are related to one another as set forth in Table 1 below, the designations X, Y and Z being those of formula I.

TABLE 1

| Mitomycin: | X | Y | Z |
|---|---|---|---|
| A | —OCH$_3$ | —OCH$_3$ | —H |
| B | —OCH$_3$ | —OH | —CH$_3$ |
| C | —NH$_2$ | —OCH$_3$ | —H |

Mitomycins are derived from mitosane compounds having the following skeleton (II):

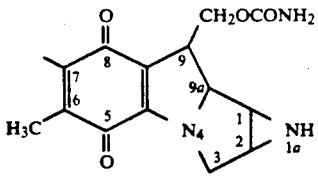

The mitosanes are formed during the cultivation of the microorganism *Streptomyces caespitosus* in a liquid nutrient medium under artificially controlled conditions. After separating the resulting mycellium, the various mitomycins may be isolated from the latter by active carbon or preferably non-ion exchange resin adsorption, organic solvent extraction or chromatography on alumina, as disclosed in U.S. Pat. No. 3,660,578 to Hata et al.

Although the mitosanes are excellent antibiotics, they have limited utility due to their toxicity to human blood (see U.S. Pat. No. 3,450,705 to Matsui et al.). The relatively highly toxic nature of the compounds has prompted search for derivatives of mitomycin to increase the antibiotic activity and to decrease toxicity.

For example, Matsui et al., U.S. Pat. No. 3,450,705, disclose mitomycin compounds substituted at the 7-position with amino, lower alkylamino, phenylamino, or pyridyl, and substituted at the 1a position with haloalkanoyl, halobenzoyl, nitrobenzoyl, alkenoyl, acetyl, glycyl, sorboyl, or acetyl methionyl.

Matsui et al., U.S. Pat. No. 3,558,651, disclose mitosane derivatives comprising 1a-acyl-7-acyloxy-9a-methoxy compounds.

Certain mitomycins and mitomycin derivatives also possess antitumor activity. Oboshi et al., *Gann* 58: 315–321 (1967); Usubuchi et al., *Gann* 58: 307–313 (1967); Matsui et al., *J. Antibiotics* XXI: 189–198 (1968); Japanese Patent No. 68 06 627 to Matsui et al. (*Chemical Abstracts* 69: 86986k (1968)); and Cheng et al., *J. Med. Chem.* 20: 767–770 (1977).

While mitomycin C is active against a relatively broad spectrum of experimental tumors, its toxicity and myelosuppressive effects limit its use in clinical practice (*Mitomycin C: Current Status and New Developments*, Carter et al. (eds.), Academic Press, New York (1979)). In preclinical and clinical studies, mitomycin C has shown activity against a variety of murine and human neoplasms, but has also shown severe, delayed bone marrow toxicity. Goldin, A., et al., *NCI-EORTC Symposium on Mitomycin C*, Brussels, Belgium (1981).

In other studies, a combination of 5-fluorouracil, adriamycin and mitomycin C was found to be effective for the treatment of patients with advanced gastric and colorectal cancer. This regimen incorporated mitomycin C administration in a single dose schedule every two months, to decrease the treatment-limiting delayed myelosuppressive effects of the compound. Schein, P.S., et al., *Mitomycin C: Current Status and New Developments*, pp. 133–143, Carter et al. (eds.), Academic Press, New York (1979).

Numerous synthetic derivatives of mitomycin C have been prepared in the hope of obtaining compounds with improved therapeutic properties. These derivatives include substitution on the aziridine ring, carbamoyl, or acyl group substitution on the hydroxymethyl side chain, and replacement of the 7-substituent in the quinone ring with other functional groups, especially substituted amines. However, as disclosed by Remers, U.S. Pat. No. 4,268,676, none of these analogs have emerged as a clinical agent, with the possible exception of the 7-hydroxy analog of the mitomycin C, which has been involved in a recent study in Japan. This analog is asserted to be less leukopenic than mitomycin C, but is also less potent. Also disclosed by Remers, supra, are totally synthetic mitomycin analogs of the mitosane type (Mott et al., *J. Med. Chem.* 21: 493 (1978)), prepared mainly for their antibacterial activity.

Kinoshita, S., et al., *J. Med. Chem.* 14: 103–112 (1971), disclose several derivatives of mitomycin substituted in the 1a, 7, and 9a positions. In particular, compounds substituted at the 1a position with sulfonyl, ortho-substituted benzoyl, and acyl derivatives were reported.

Iyengar, B.S., et al., *J. Med. Chem.* 24: 975–981 (1981), disclose a series of 31 mitomycin C and porfiromycin analogues with various substituents at the 7- and 1a-positions. The most active substituents at the 7-position included aziridine, 2-methylaziridine, proparylamine, furfurylamine, methyl glycinate and 3-aminopyridine.

Iyengar, B., et al., *J. Med. Chem.* 26: 16–20 (1983), disclose a series of 7-substituted mitomycin C and porfiromycin derivatives and the screening thereof in standard antitumor systems. The authors report that the 7-position controls the reduction of the quinone ring, thus suggesting that it would be possible to alter the substitution of the 7-position to gain selectivity between normal cells and certain cancer cells.

Iyengar, B.S., et al., *J. Med. Chem.* 26: 1453-1457 (1983), disclose 20 mitomycin C analogues substituted with secondary amines at the 7-position. Eleven of these analogues were more active than mitomycin C against P388 murine leukemia and two of these eleven were significantly less leukopenic. The authors report that no quantitative correlation between antitumor activity and physiochemical properties of the analogues was evident, although the relative ease of quinone reduction may be related to activity.

Iyengar, B.S., et al., *J. Med. Chem.* 29: 1864-1868 (1986), disclose the preparation of 7-substituted amino 1,2-aziridinomitosenes. The authors reported that a methyl group on the aziridine nitrogen gave increased potency. The 7-amino mitosene derivatives which were difficult to reduce to hydroquinones were essentially inactive.

Sami, S., et al., *J. Med. Chem.* 27: 701-708 (1984), disclose a series of 30 $N^7$-phenyl-substituted mitomycin C analogs. Two of the compounds having pyrazolyl or aminopyridyl substituents at the 7-position were disclosed as clearly superior to mitomycin C in activity against P388 murine leukemia.

Sami, T., et al., *J. Med. Chem.* 22: 247-250 (1979), also disclose N-(2-chloroethyl)-N-nitrosocarbamoyl derivatives of glycosylamines, including three disaccharide derivatives which exhibited strong antitumor activity against leukemia 1210 in mice. In addition, glucopyranose derivatives of N-nitrosoureas possess immunogenic and marrow-sparing properties. Anderson et al., *Cancer Research* 35: 761-765 (1975); Panasci et al., *J. Clin. Invest.* 64: 1103-1111 (1979).

In U.S. Pat. No. 4,720,543, compounds having the following general Formula (III) are disclosed:

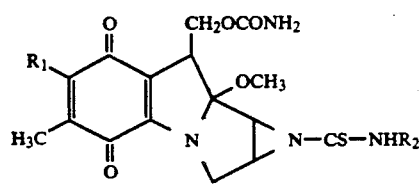

where
  $R^1$ is selected from the group consisting of $NH_2$, $C_1$-$C_4$ alkoxy and a glycosyl residue; and
  $R^2$ is selected from the group consisting of H, $C_1$-$C_4$ alkyl, and a glycosyl residue, with the proviso that either $R_1$ or $R_2$, but not both, contain a glycosyl group.

The compounds represented by Formula (III) have excellent anti-neoplastic activity and at the same time possess reduced bone marrow toxicity and lower overall toxicity.

Despite the above-listed mitomycin derivatives, a need continues to exist for improved mitomycin derivatives having good anti-neoplastic properties and low bone marrow and overall toxicity.

SUMMARY OF THE INVENTION

The invention relates to a mitomycin derivative having the following general Formula (IV):

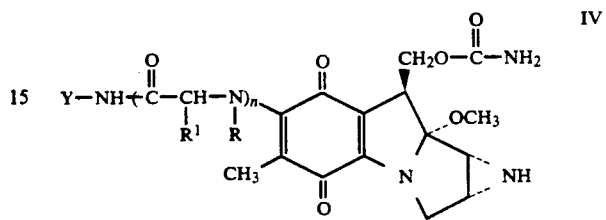

wherein
n is 0 or 1;
Y is selected from the group consisting of glucopyranosyl, galactopyranosyl, mannopyranosyl, xylopyranosyl, cellobiosyl, lactosyl, glucofuranosyl, maltosyl, and 2-amino-1,3-cyclohexanediol, or a hydroxyl-protected derivative thereof or the corresponding aminosaccharide, diaminosaccharide or triamino saccharide;
R is hydrogen;
$R^1$ is hydrogen, $C_1$-$C_4$ alkyl or $C_1$-$C_4$ alkyl substituted by phenyl, hydroxyphenyl, indolyl, mercapto, $C_1$-$C_4$ alkylthio, hydroxy, carboxy, amino, guanidino, imidazole or carbamyl; or
R and $R^1$ together form a five or six membered nitrogen containing ring.

The invention also relates to a mitomycin derivative having the following general Formula (V):

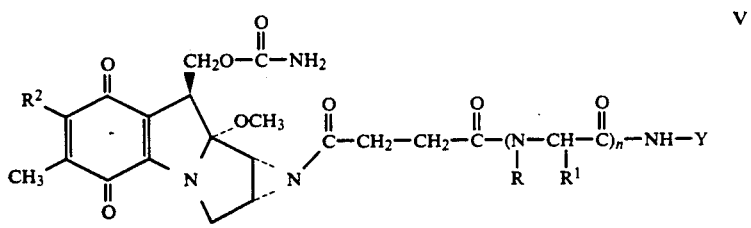

wherein n, R, $R^1$ and Y are as defined above and $R^2$ is $NH_2$— or $CH_3O$—.

The invention also relates to a mitomycin derivative having the following structural Formula (VI):

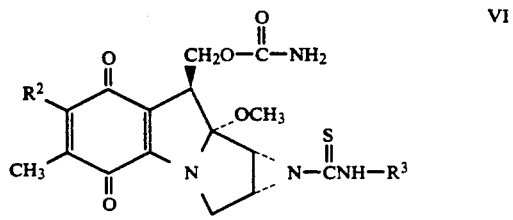

wherein
$R^2$ is $NH_2$— or $CH_3O$—; and $R^3$ is a 2-(3-cyano-4-morpholinyl)-2-deoxypyranosyl saccharide or a 2-(4-morpholinyl)-2-deoxypyranosyl saccharide.

The invention also relates to a mitomycin derivative having the following structural Formula (VII):

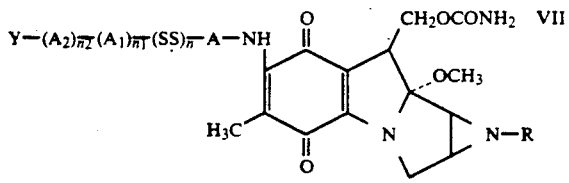

wherein

R is hydrogen, $C_1$-$C_4$ straight or branched alkyl;

A is $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;

n is 0 or 1;

$n_1$ is 0 or 1;

$A_1$ is oxygen, $C_1$-$C_4$ straight or branched saturated or unsaturated alkylene, —C(=O)—NH—, or —NH—C(=O)—;

$A_2$ is oxygen, $C_1$-$C_4$ straight or branched saturated or unsaturated alkylene, NH, NR, or —NH—C(=O)—;

$n_2$ is 0 or 1;

Y is selected from the group consisting of glucopyranosyl, galactopyranosyl, mannopyranosyl, xylopyranosyl, cellobiosyl, lactosyl, glucofuranosyl, maltosyl, and 1,3-cyclohexanediol-2-yl, or a hydroxyl-protected derivative thereof or the corresponding aminosaccharide, diaminosaccharide or triaminosaccharide; or branched saturated or unsaturated alkylene; with the further proviso that when n is 0, then one of $n_1$ and $n_2$ is 0.

The invention also relates to a mitomycin derivative having the Formula (VIII):

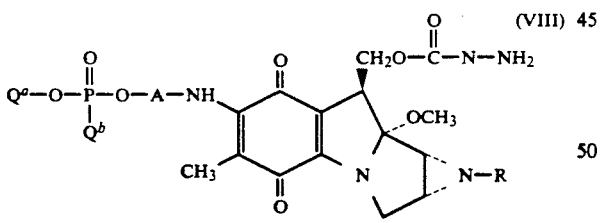

wherein

R is hydrogen, $C_1$-$C_4$ straight or branched alkyl,

A is $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;

$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the Formula (IX):

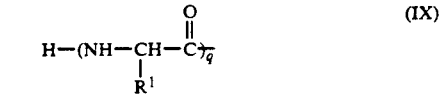

wherein $R^1$ is hydrogen, $C_1$-$C_4$ alkyl, or $C_1$-$C_4$ alkyl substituted by phenyl, hydroxyphenyl, indolyl, mercapto, $C_1$-$C_4$ alkylthio, hydroxy, carboxy, amino, guanidino, imidazolyl or carbamoyl;

q=0–4;

The invention also relates to a mitomycin derivative having the Formula (X):

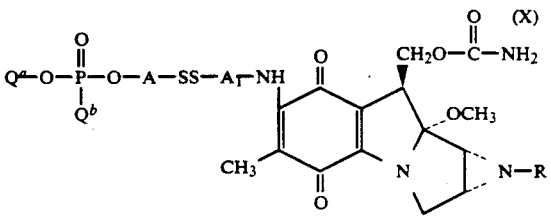

wherein

R is hydrogen, $C_1$-$C_4$ straight or branched alkyl,

A and $A_1$ are $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;

$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the Formula (IX):

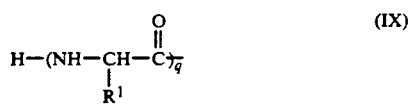

wherein $R^1$ is hydrogen, $C_1$-$C_4$ alkyl, or $C_1$-$C_4$ alkyl substituted by phenyl, hydroxyphenyl, indolyl, mercapto, $C_1$-$C_4$ alkylthio, hydroxy, carboxy, amino, guanidino, imidazolyl or carbamoyl;

q=0–4.

The invention also relates to a process for preparing a mitomycin derivative having the Formula (IVA)

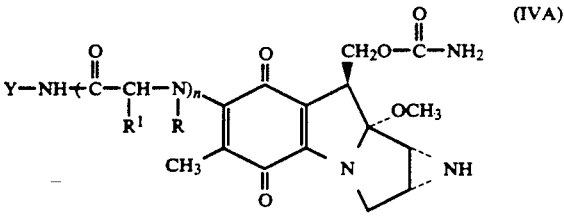

wherein n is 1;

Y is selected from the group the group consisting of glucopyranosyl, galactopyranosyl, mannopyranosyl, xylopyranosyl, cellobiosyl, lactosyl, glucofuranosyl, maltosyl, and 1,3-cyclohexanediol-2-yl, or a hydroxyl-protected derivative thereof or the corresponding aminosaccharide, diaminosaccharide or triaminosaccharide;

R is hydrogen;

$R^1$ is hydrogen, $C_1$–$C_4$ alkyl or $C_1$–$C_4$ alkyl substituted by phenyl, hydroxyphenyl, indolyl, mercapto, $C_1$–$C_4$ alkylthio, hydroxy, carboxy, amino, guanidino, imidazole or carbamyl; or R and $R^1$ together form a five or six membered nitrogen containing ring;

comprising:

(a) condensing an N-protected amino acid with an alcohol in the presence of a dehydration reagent to give an activated ester, (b) condensing the activated ester obtained in step (a) with an amino compound to give a protected amino acid-amino compound conjugate, (c) removing the protecting group of the protected amino acid-amino compound conjugate obtained in step (b) to give an amino acid-amino compound conjugate, and (d) condensing the amino acid-amino compound conjugate obtained in step (c) with mitomycin A to give the mitomycin derivative.

The invention also relates to a process for the preparation of a mitomycin derivative having the Formula (VIA):

(VIA)

wherein $R^2$ is $NH_2$— or $CH_3O$—; and $R^3$ is a 2-(3-cyano-4-morpholinyl)-2-deoxy saccharide;

comprising (a) condensing bis(acetaldehyde-2-yl) ether with a 2-amino-2-deoxy saccharide in the presence of a salt of cyanoborohydride to give a 2-deoxy-2-(3-cyano-4-morpholinyl) saccharide and a 2-deoxy-4-morpholinyl saccharide;

(b) separation of the 2-deoxy-2-(3-cyano-4-morpholinyl) saccharide from the 2-deoxy-4-morpholinyl saccharide obtained in step (a);

(c) reaction of the 2-deoxy-2-(3-cyano-4-morpholinyl) saccharide obtained in step (b) with an acetyl halide to give a 2-deoxy 1-halo-2-(3-cyano-4-morpholinyl) peracetyl saccharide;

(d) treatment of the 2-deoxy-1-halo-2-(3-cyano-4-morpholinyl) peracetyl saccharide obtained in step (c) with silver thiocyanate to give a saccharide-1-thiocyanate;

(e) reaction of the saccharide-1-thiocyanate obtained in step (d) with mitomycin C or mitomycin A to give a mitomycin C- or mitomycin A-saccharide peracetate carbothioamide; and (f) hydrolysis of the acetate groups of the mitomycin-C-saccharide peracetate obtained in step (e) to give the mitomycin derivative.

The invention also relates to a process for the preparation of a mitomycin derivative having the following Formula (VIB)

(VIB)

wherein $R^2$ is $NH_2$— or $CH_3O$—; and $R^3$ is a (4-morpholinyl)-2-deoxy saccharide;

comprising:

(a) condensation of bis(acetaldehyde-2-yl) ether with a 2-amino-2-deoxy saccharide in the presence of a salt of cyanoborohydride to give a 2-deoxy-2-(3-cyano-4-morpholinyl) saccharide and a 2-deoxy-2-(4-morpholinyl) saccharide;

(b) separation of said 2-deoxy-2-(4-morpholinyl) saccharide from said 2-deoxy-2-(3-cyano-4-morpholinyl) saccharide obtained in step (a);

(c) reaction of the 2-deoxy-2-(4-morpholinyl) saccharide obtained in step (b) with an acetyl halide to give a 2-deoxy-1-halo-2-(4-morpholinyl) peracetyl saccharide;

(d) treatment of the 2-deoxy-1-halo-2-(4-morpholinyl) peracetyl saccharide obtained in step (c) with silver thiocyanate to give a saccharide-1-thiocyanate;

(e) reaction of the saccharide-1-thiocyanate obtained in step (d) with mitomycin A or C to give a mitomycin A- or C-saccharide peracetate carbothioamide; and (f) hydrolysis of the acetate groups of the mitomycin-C-saccharide peracetate obtained in step (e) to give the mitomycin derivative.

The invention also relates to a process for the preparation of a mitomycin derivative having the following Formula (VA)

(VA)

wherein n is 0 or 1;

Y is selected from the group consisting of glucopyranosyl, galactopyranosyl, mannopyranosyl, xylopyranosyl, cellobiosyl, lactosyl, glucofuranosyl, maltosyl, and 1,3-cyclohexanediol-2-yl or the corresponding aminosaccharide, diaminosaccharide or triaminosaccharide;

R is hydrogen;

$R^1$ is hydrogen, $C_1-C_4$ alkyl or $C_1-C_4$ alkyl substituted by phenyl, hydroxyphenyl, indolyl, mercapto, $C_1-C_4$ alkylthio, hydroxy, carboxy, amino, guanidino, imidazole or carbamyl; or R and $R^1$ together form a five or six membered nitrogen containing ring;

$R^2$ is $NH_2$—;

comprising:

(a) condensation of mitomycin C with succinic anhydride under basic conditions to give a mitomycin C-la-succinic acid ester;

(b) condensation of the mitomycin C-la-succinic acid ester obtained in step (a) with a compound of the Formula (XI):

$$H(N-CH-\underset{R}{\overset{O}{\overset{\|}{C}}})_n-NH-Y^P \qquad XI$$
$$\phantom{H(N-CH}\underset{R}{|}\phantom{-\overset{O}{\overset{\|}{C}})_n-NH-}\underset{R^1}{|}$$

wherein R, $R^1$ and n are defined above and $Y^P$ is a hydroxyl-protected saccharide selected from the group consisting of the hydroxyl-protected derivatives of glucopyranosyl, galactopyranosyl, mannopyranosyl, xylopyranosyl, cellobiosyl, lactosyl, glucofuranosyl, maltosyl, and 1,3-cyclohexanediol-2-yl or the corresponding aminosaccharide, diaminosaccharide or triaminosaccharide;

(c) removal of the hydroxyl protecting groups to give the mitomycin derivative.

The invention also relates to a process for the preparation of a mitomycin derivative having the following Formula (VB):

(VB)

[structure diagram]

wherein n is 0 or 1;

Y is selected from the group consisting of glucopyranosyl, galactopyranosyl, mannopyranosyl, xylopyranosyl, cellobiosyl, lactosyl, glucofuranosyl, maltosyl, and 1,3-cyclohexanediol-2-yl or the corresponding aminosaccharide, diaminosaccharide or triaminosaccharide;

R is hydrogen;

$R^1$ is hydrogen, $C_1-C_4$ alkyl or $C_1-C_4$ alkyl substituted by phenyl, hydroxyphenyl, indolyl, mercapto, $C_1-C_4$ alkylthio, hydroxy, carboxy, amino, guanidino, imidazole or carbamyl; or R and $R^1$ together form a five or six membered nitrogen containing ring;

$R^2$ is $CH_3O$—;

comprising:

(a) condensation of mitomycin A with succinic anhydride under basic conditions to give mitomycin A-la-succinic acid ester;

(b) condensation of the mitomycin A-la-succinic acid ester obtained in step (a) with a compound of the Formula (XI):

$$H(N-CH-\overset{O}{\overset{\|}{C}})_n-NH-Y^P \qquad XI$$
$$\phantom{H(N-}\underset{R}{|}\phantom{-}\underset{R^1}{|}$$

wherein R, $R^1$ and n are as defined above and $Y^P$ is a hydroxyl-protected saccharide selected from the group consisting of the hydroxyl-protected derivatives of glucopyranosyl, galactopyranosyl, mannopyranosyl, xylopyranosyl, cellobiosyl, lactosyl, glucofuranosyl, maltosyl, and 1,3-cyclohexanediol-2-yl, or the corresponding aminosaccharide, diaminosaccharide or triamino saccharide to give a hydroxyl protected mitomycin derivative; and (c) removal of the hydroxyl protecting groups from the compound obtained in step (b) to give the mitomycin derivative (V).

The invention also relates to a process for the preparation of a mitomycin derivative having the following Formula (VIIA):

$$Y-(A_2)_{\overline{n_2}}(A_1)_{\overline{n_1}}(SS)_{\overline{n}}-A-NH \qquad (VIIA)$$

[structure diagram]

wherein

R is hydrogen, $C_1-C_4$ straight or branched alkyl;

A is $C_1-C_4$ straight or branched alkylene or unsaturated alkylene, phenylene, substituted phenylene, benzylene (—$CH_2Ph$—), substituted benzylene, heteroaryl, substituted heteroaryl, or $C_3-C_6$-heterocycloalkyl;

n is 0;

$n_1$ is 1;

$A_1$ is oxygen;

$n_2$ is 0;

Y is selected from the group consisting of glucopyranosyl, galactopyranosyl, mannopyranosyl, xylopyranosyl, cellobiosyl, lactosyl, and glucofuranosyl, maltosyl, or a hydroxyl-protected derivative thereof or the corresponding aminosaccharide, diaminosaccharide or triaminosaccharide;

comprising:

(a) condensing an acetyl halide with a saccharide (Y—H) to give a 1-halo peracetyl saccharide;

(b) condensing the 1-halo peracetyl saccharide obtained from step (a) with a compound of the formula HO—A—$NO_2$, wherein A is defined as above, to give a nitro saccharide derivative;

(c) reducing the nitro group of the nitro saccharide derivative obtained in step (b) to obtain a primary amino saccharide;

(d) condensing the primary amino saccharide obtained in step (c) with a mitomycin A derivative of Formula (XII):

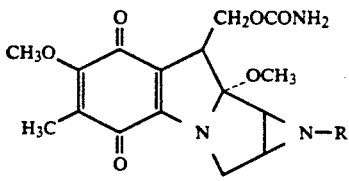

to give a mitomycin-C-saccharide peracetate; and (e) hydrolysis of the acetate groups of the mitomycin-C-saccharide peracetate obtained in step (d) to give the mitomycin derivative having Formula (VII).

The invention also relates to a process for the preparation of a mitomycin derivative having the following Formula (VIIB):

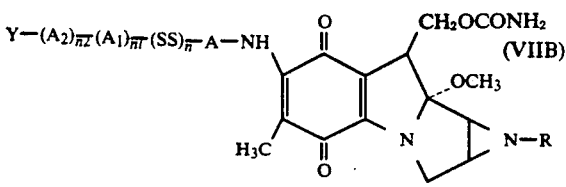

wherein
n and $n_1$ are 0;
$n_2$ is 1;
$A_2$ is —NH—C(=O)—; and
R, A, and Y are defined above;
comprising:

(a) condensing an acetyl halide with a saccharide to give a 1-halo peracetyl saccharide;

(b) condensing an azide salt with the compound obtained in step (a) to give a 1-azido saccharide derivative;

(c) reducing the 1-azido saccharide derivative obtained in step (b) to obtain a 1-primary amino saccharide;

(d) condensing the 1-primary amino saccharide obtained in step (c) with a compound of the formula PhCH$_2$OC(=O)NH—A—C(=O)OH to give a benzyloxycarbonyl protected saccharide derivative;

(e) reducing the benzyloxycarbonyl protected saccharide derivative formed in step (d) to form a compound of the formula Y—NH—C(=O)—A—NH2;

(f) condensing the compound of the formula Y—NH—C(=O)—A—NH2 obtained in step (e) with a mitomycin A derivative of the Formula (XII):

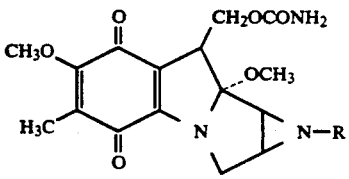

to give a peracetyl saccharide-linked mitomycin derivative; and (g) hydrolysis of the acetate groups of the peracetyl saccharide-linked mitomycin derivative obtained in step (f) to give the mitomycin derivative having Formula (VII).

The invention also relates to a process for the preparation of a mitomycin derivative having the following Formula (VIIC):

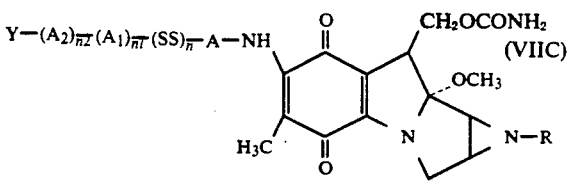

wherein
n is 1;
$n_1$ is 0 or 1;
$n_2$ is 0;
$A_1$ is a $C_1$-$C_4$ straight or branched saturated or unsaturated alkylene;
comprising:

(a) condensing a hydroxy protected compound of the formula Y—(A$_1$)$_{n1}$—SH with a compound of the formula CH$_3$—O—C(=O)—SS—A—NH$_2$ to give Y—(A$_1$)$_{n1}$—SS—A—NH$_2$;

(b) condensing Y—(A$_1$)$_{n1}$—SS—A—NH$_2$ obtained in step (a) with a mitomycin A derivative of the Formula (XII):

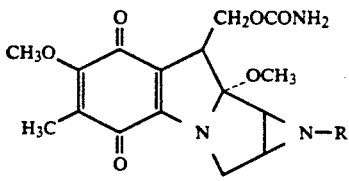

to give a hydroxyl protected saccharide-linked mitomycin derivative; and (c) removal of the protecting groups of the hydroxyl protected saccharide-linked mitomycin derivative obtained in step (b) to give the mitomycin derivative (VII).

The invention also relates to a process for the preparation of a mitomycin derivative having the Formula (VIII):

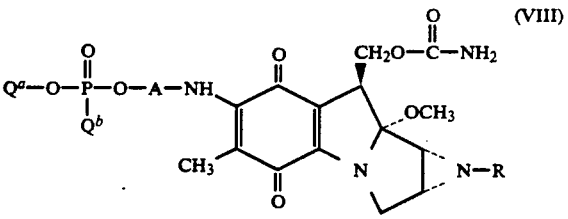

wherein
R is hydrogen, $C_1$-$C_4$ straight or branched alkyl,
A is $C_1$-$C_4$ straight or branched alkylene or unsaturated alkylene, phenylene, substituted phenylene, benzylene. (—CH$_2$Ph—), substituted benzylene, heteroaryl, substituted heteroaryl, or $C_3$-$C_6$-heterocycloalkyl;
$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the Formula (IX):

$$H-(NH-CH-C)_{\overline{q}} \quad (IX)$$
$$\quad\quad\quad\quad |$$
$$\quad\quad\quad\quad R^1$$

wherein $R^1$ is hydrogen, $C_1-C_4$ alkyl, or $C_1-C_4$ alkyl substituted by phenyl, hydroxyphenyl, indolyl, mercapto, $C_1-C_4$ alkylthio, hydroxy, carboxy, amino, guanidino, imidazolyl or carbamoyl;

$q=0-4$;

comprising condensing a compound of Formula (XIII):

$$Q^a-O-\overset{O}{\underset{Q^b}{\overset{\|}{P}}}-O-A-NH_2 \quad (XIII)$$

with a mitomycin A derivative of the Formula (XII):

(XII) — structure with $CH_3O$, $CH_2OCONH_2$, $OCH_3$, $H_3C$, N, N—R

The invention also relates to a process for preparing a mitomycin derivative having the Formula (X):

(X) — structure with $Q^a-O-\overset{O}{\underset{Q^b}{\overset{\|}{P}}}-O-A-SS-A_1-NH$, $CH_2O-\overset{O}{\overset{\|}{C}}-NH_2$, $OCH_3$, $CH_3$, N, N—R wherein R is hydrogen, $C_1-C_4$ straight or branched alkyl, A and $A_1$ are $C_1-C_4$ straight or branched alkylene or unsaturated alkylene, phenylene, substituted phenylene, benzylene (—$CH_2Ph$—), substituted benzylene, heteroaryl, substituted heteroaryl, or $C_3-C_6$-heterocycloalkyl;

$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the Formula (IX):

$$H-(NH-CH-C)_{\overline{q}} \quad (IX)$$
$$\quad\quad\quad\quad |$$
$$\quad\quad\quad\quad R^1$$

wherein $R^1$ is hydrogen, $C_1-C_4$ alkyl, or $C_1-C_4$ alkyl substituted by phenyl, hydroxyphenyl, indolyl, mercapto, $C_1-C_4$ alkylthio, hydroxy, carboxy, amino, guanidino, imidazolyl or carbamoyl;

$q=0-4$;

comprising condensing a compound having the Formula (XIV):

$$Q^a-O-\overset{O}{\underset{Q^b}{\overset{\|}{P}}}-O-A-SS-A_1-NH_2 \quad (XIV)$$

with a mitomycin A derivative having the Formula (XII):

(XII) — structure with $CH_3O$, $CH_2OCONH_2$, $OCH_3$, $H_3C$, N, N—R

The invention also relates to pharmaceutical compositions comprising a therapeutically effective amount of the mitomycin derivatives of the invention together with a pharmaceutically acceptable carrier.

The invention also relates to methods for the treatment of bacterial infections comprising administering the pharmaceutical compositions of the invention to an animal.

The invention also relates to methods for the treatment of cancer by suppressing growth of cancer cells susceptible to growth suppression comprising administering the pharmaceutical compositions of the invention to an animal.

DESCRIPTION OF THE PREFERRED EMBODIMENTS

Figure 1:
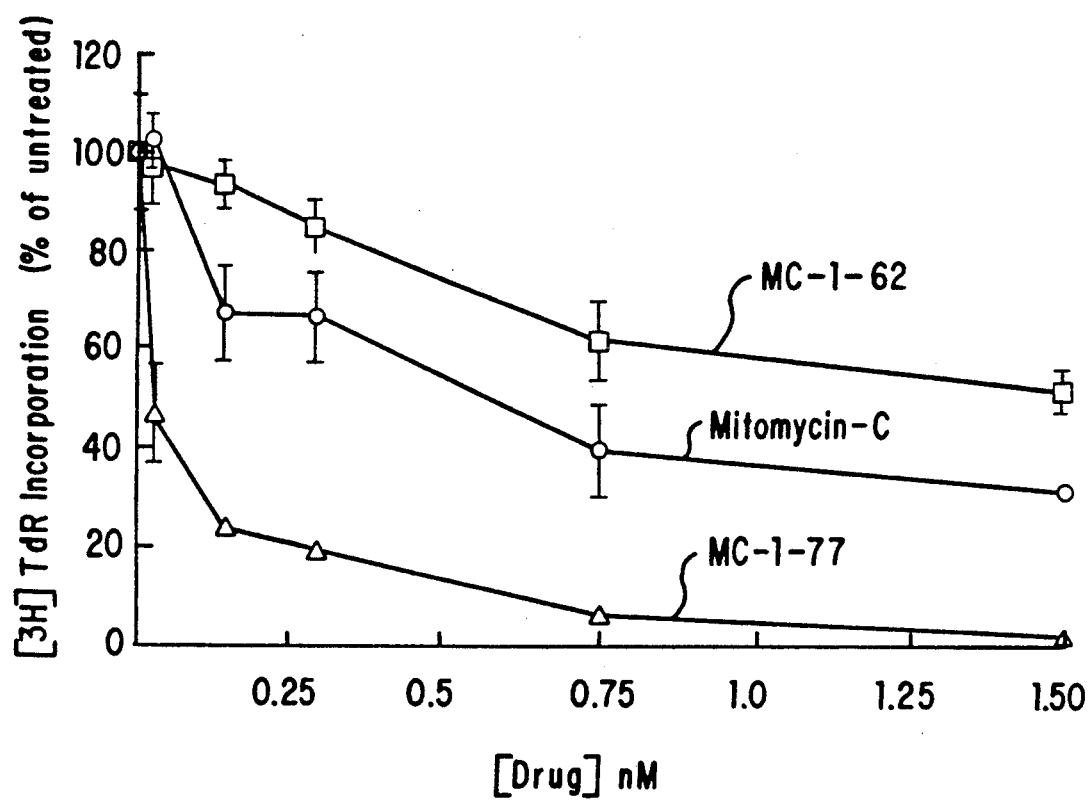
FIG. 1 depicts a graph showing the response of the MDA-MB-231 human breast tumor cell line to several concentrations of the drugs mitomycin-C, MC-1-77, and MC-1-62.

The synthetic preparation of the mitomycin derivatives of the invention have, as their starting point, mitomycin C. Mitomycin C may be prepared according to the methods generally disclosed in Cheng et al., *J. Med. Chem.* 20:767–770 (1977). Alternatively, mitomycin C can be obtained from mitomycin A by treatment of mitomycin A with a methanolic-ammonia solution as described by Matsui, M., et al., *J. Antibiotics* XXI:189 (1968).

The mitomycin derivatives of Formula (IV), wherein n=0 (XVI), may be obtained by displacement of the methoxy group of mitomycin A (XII) with the amino group of an amino compound, for example, glucosamine (Y—NH$_2$; (XV)) under basic conditions in a polar organic solvent to give the N$^7$-substituted mitomycin derivative (XVI) (see Scheme I below).

Amino compounds (Y—NH$_2$) which may be substituted at the 7-position include, but are not limited to glucosamine, galactosamine, mannosamine, xylosamine, cellobiosamine, maltosamine and 2-amino-1,3-cyclohexanediol and the hydroxyl-protected derivatives thereof. Preferably, the saccharide comprising the group "Y" is substituted at the 2-position with the amino group. Polar organic solvents which may be used in the practice of the invention include methanol, ethanol, propanol, dimethylsulfoxide, and dimethylformamide. Suitable bases for providing the basic conditions of the reaction include alkylamines such as C$_1$-C$_3$ trialkyl amines, diisopropylethylamine, 1,8-diazabicyclo[5.4.-0]undec-7-ene (DBU) and dimethylaminopyridine (DMAP). In general, mitomycin A and the amino derivative are present in a 1:1 molar ratio, although excess amino derivative may be present. Sufficient base is present in the reaction mixture to insure that the reaction remains basic throughout.

Preferred mitomycin derivatives having Formula XVI include N$^7$-(2-deoxyglucopyranosyl)mitomycin C, N$^7$-(2-deoxygalactopyranosyl)mitomycin C, N$^7$-(tetraacetyl-2-deoxyglucopyranosyl)mitomycin C, and N$^7$-(tetraacetyl-2-deoxygalactopyranosyl)mitomycin C.

Scheme I

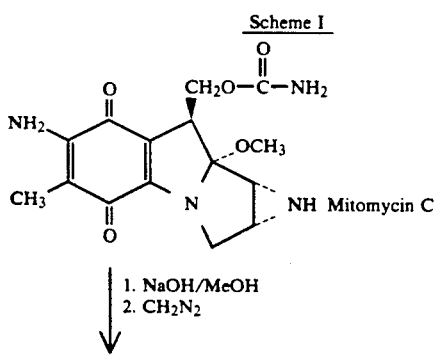

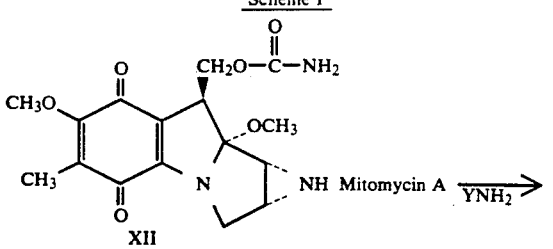

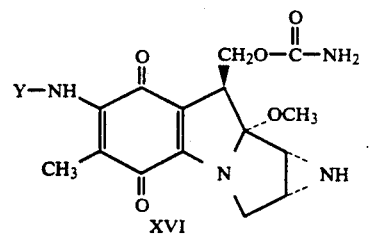

The amino acid linked mitomycin derivatives of Formula (IV), wherein n=1, may be prepared (Scheme II) from mitomycin A by condensation of the N-protected amino acid, for example, the N-benzyloxycarbonyl derivative (XVII), with an alcohol such as N-hydroxysuccinamide, which is capable of generating an activated ester, and a dehydrating reagent to give the activated ester (XVIII). Dehydrating reagents which may be used in this process include, but are not limited to dicyclohexylcarbodiimide (DCC) and diethylazodicarboxylate (DEAD) and triphenylphosphine. Treatment of the activated ester (XVIII) with any of the above-listed amino compounds (XV) gives the protected amino acid-amino compound conjugate (XIX). Removal of the protecting group, for example, by hydrogenolysis of the N-benzyloxycarbonyl group, gives the free amino derivative (XX). Compound (XX) may then be condensed with mitomycin A (XII) by displacement of —OCH$_3$ as described above to give the amino acid linked mitomycin derivative (IV).

Preferred mitomycin derivatives having Formula (IV), wherein n=1, R$^1$=H and R=H include N$^7$-[[[(2-deoxy-2-glucopyranosyl)amino]carbonyl]methyl] mitomycin C and N$^7$-[[[(tetraacetyl-2-deoxy-2-glucopyranosyl)amino]carbonyl]methyl]mitomycin C.

Scheme II

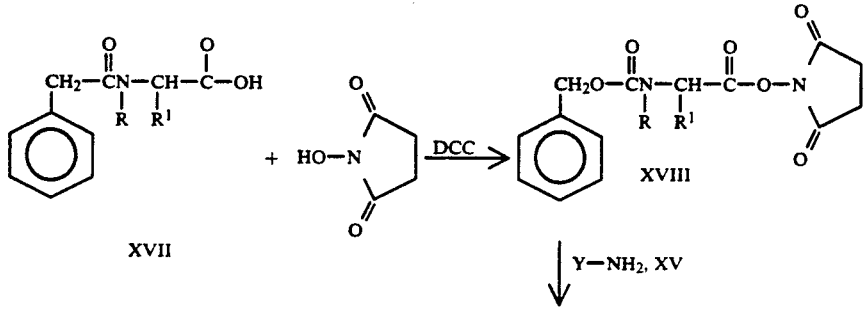

Scheme II -continued

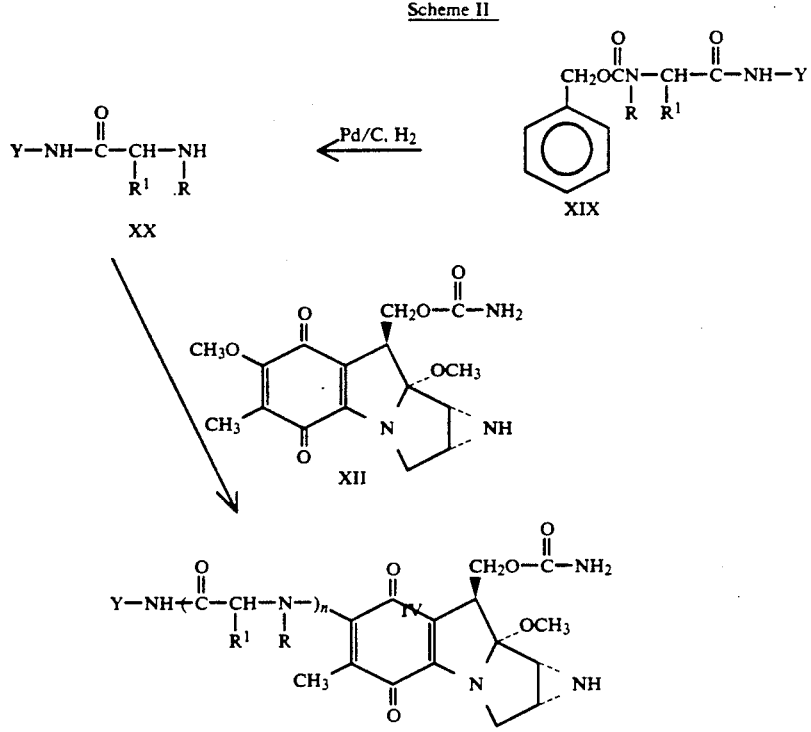

Mitomycin derivatives having Formula (V), wherein $R^2$ is $NH_2$ and n is 0 (Formula (XXI), below), may be prepared (Scheme III) by condensation of mitomycin C Preferred mitomycin derivatives having Formula (XXV) include $N^1$-[[2-[[(2-deoxy-2-glucopyranosyl-)amino]carbonyl]ethyl]carbonyl] mitomycin C.

Scheme III

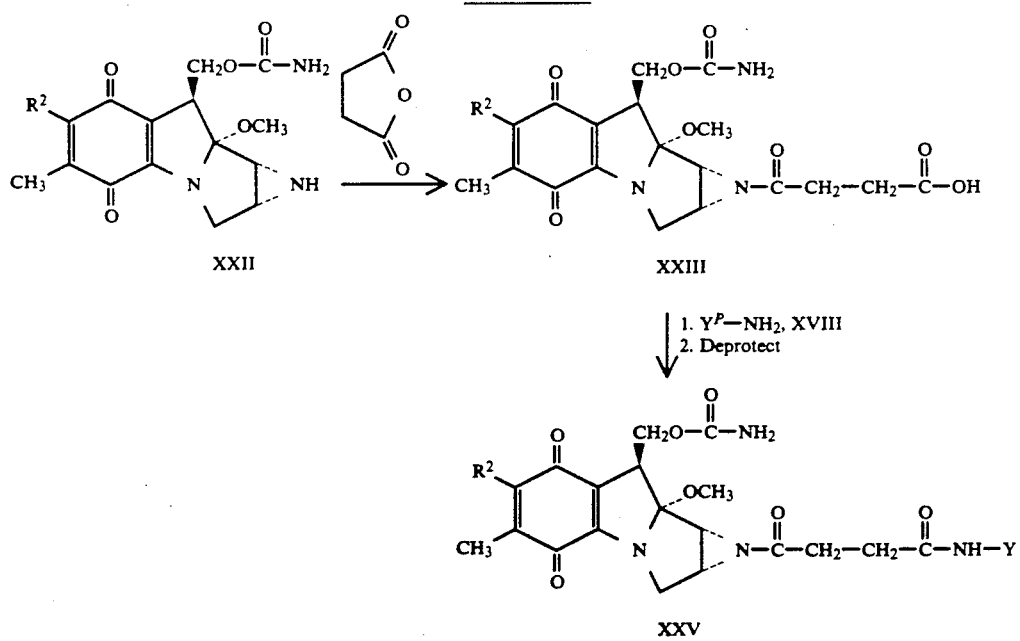

(XXII) with succinic anhydride to give the amide (XXIII) which may then be condensed with the hydroxyl-protected amino derivative $Y^P$-$NH_2$ (XXIV) using any of the above-listed dehydrating reagents followed by deprotection to give (XXV). Protecting groups for the amino derivative include, but are not limited to, $C_2$-$C_4$ acyl esters.

Mitomycin derivatives having Formula (V), wherein $R^2$ is —$OCH_3$ and n is 0 (Formula (XIX), below), may be prepared (Scheme IV) by treatment of mitomycin C (XXII) with sodium methoxide in absolute methanol to give mitomycin A (XII) followed by condensation with succinic anhydride to give the mitomycin A-1a-succinic acid ester (XXVI). Condensation of the carboxylic acid group of (XXVI) with the hydroxyl-protected amino derivative $Y^p$-NH$_2$ (XIV), as described above, followed by deprotection gives (XXVII).

Preferred mitomycin derivatives having Formula XXVII include $N^1$-[[2-[[(2-deoxy-2-glucopyranosyl)amino]carbonyl]ethyl]carbonyl] mitomycin A.

column chromatography. Salts of cyanoborohydride may include any of the alkali metal salts of cyanoborohydride, preferably sodium cyanoborohydride. Treatment of the saccharide derivative (XXXIa) with an acetyl halide gives the 2-deoxy-1-halo-(4-morpholinyl) peracetyl saccharide which may be reacted with silver

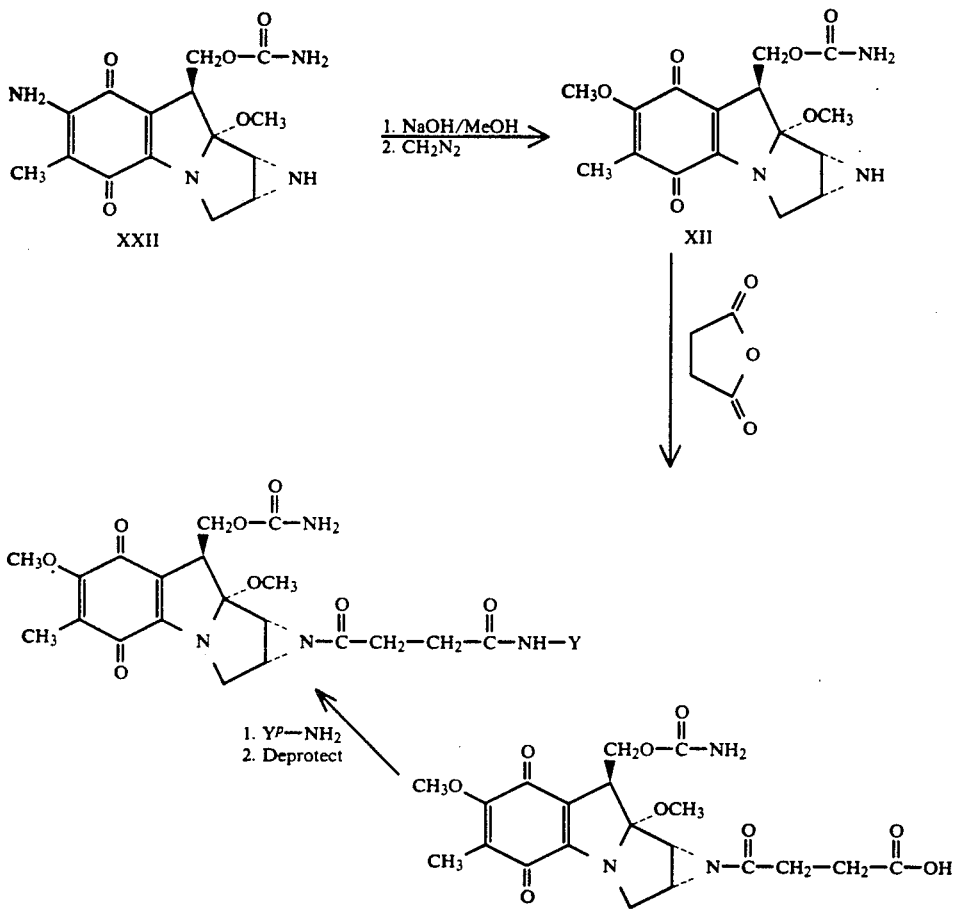

The mitomycin derivatives of Formula VI may be prepared according to the sequence depicted in Scheme V. Treatment of 3,4-dihydroxytetrahydrofuran (XXVIII) with aqueous sodium periodate in a polar organic solvent gives bis(acetaldehyde-2-yl) ether (XXIX) which may be condensed with a 2-amino-2-deoxy-saccharide (XXX) in the presence of a salt of cyanoborohydride to give a mixture of 2-deoxy-2-(3-cyano-4-morpholino) saccharide ((XXXIa), Q=—CN), and 2-deoxy-4-morpholinyl saccharide ((XXXIb), Q=—H) which may be separated, for example, by thiocyanate to give a 1-thiocyanate saccharide (XXXII). Condensation of the thiocyanate (XXXII) with mitomycin C (XXII) gives the mitomycin C-saccharide peracetate carbothioamide (XXXIII). Deacylation of (XXXII), for example, with methanolic ammonia, gives (VI) (Q=—CN or H).

Preferred mitomycin derivatives having Formula VI include 2-(3-cyano-4-morpholinyl) 2-deoxyglucopyranosyl mitomycin-1a-carbothioamide and 2-(3-cyano-4-morpholinyl)-2-deoxygalactopyanosylmitomycin-1a-carbothioamide.

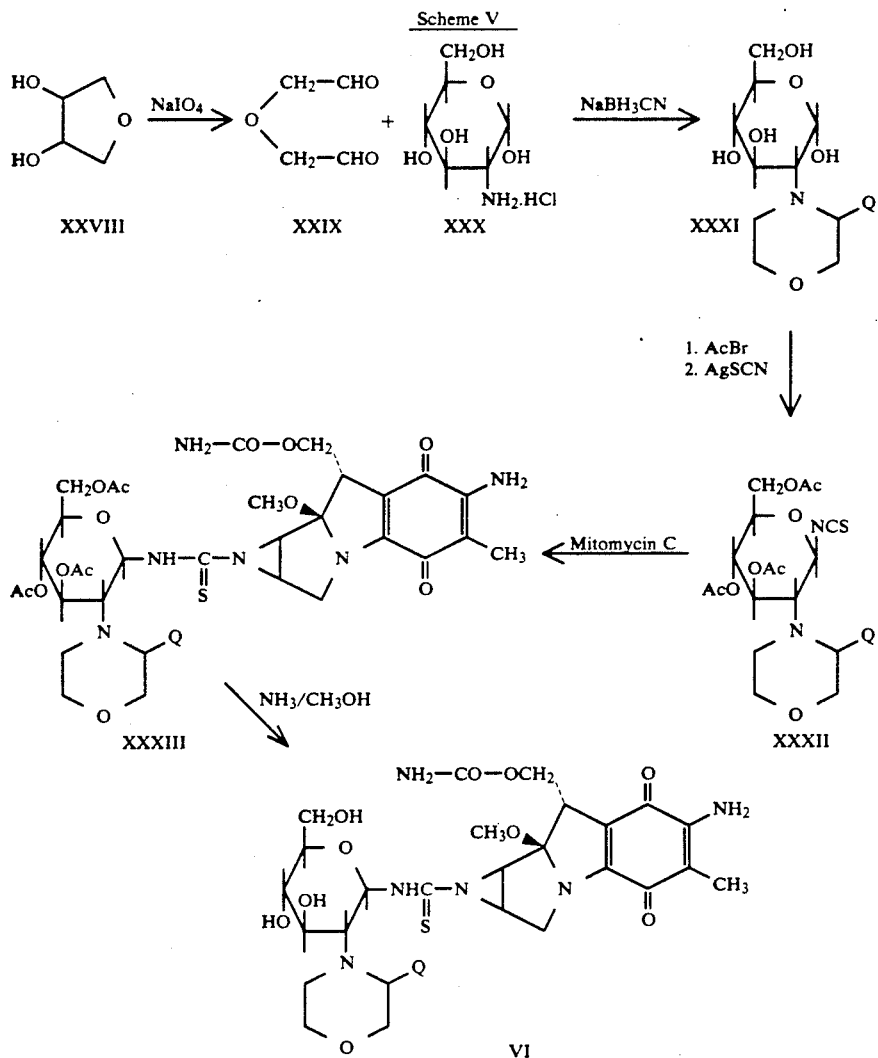

Mitomycin derivatives of Formula VII may be prepared according to the reaction sequences depicted in Schemes VI, VII, and VIII. As shown in Scheme VI, a saccharide (XXXIV) is first reacted with an acetyl halide to form a 1-halo peracetyl saccharide (XXXV). This compound is then condensed with p-nitrophenol to give (XXXVI). Reduction of the nitro group with a hydrogenation catalyst such as palladium on carbon and hydrogen gives the aniline derivative (XXXVII). Condensation of (XXXVII) with the mitomycin A derivative (XII) gives the mitomycin derivative (XXXVIII).

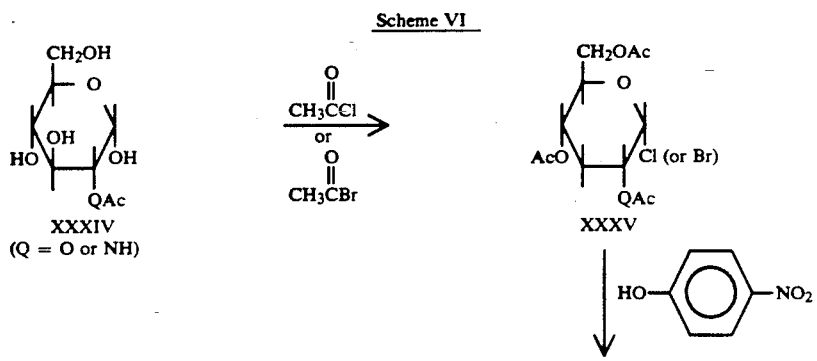

Scheme VI

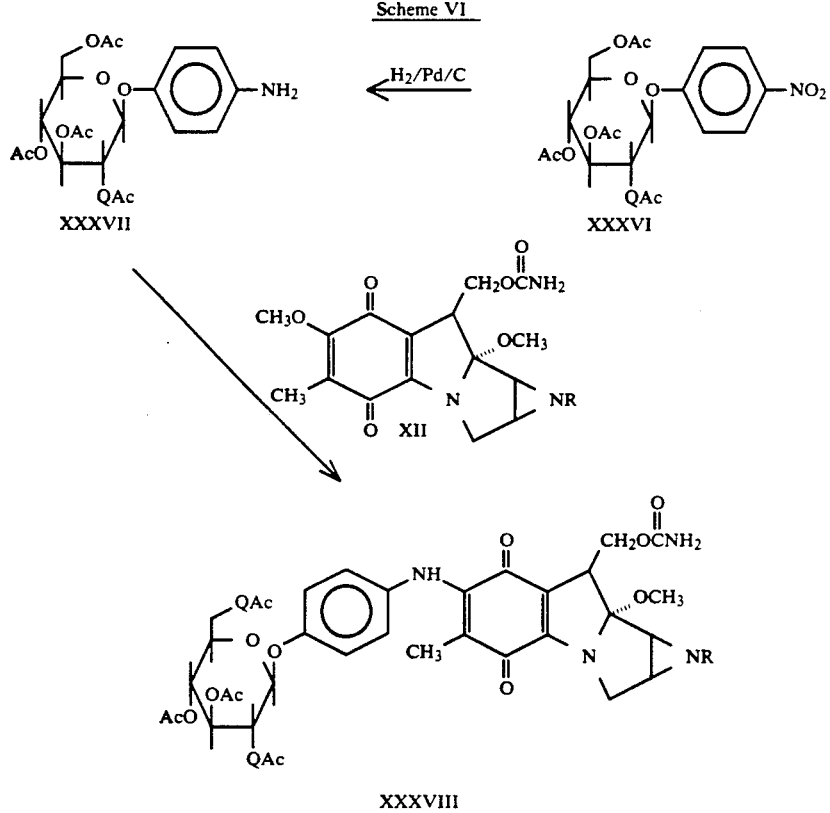

Alternatively, the 1-halo peracetyl saccharide (XXXIX) (see Scheme VII) can be reacted with an azide salt to give the anomeric azide (XXXX). Catalytic hydrogenation of (XXXX) using a hydrogenation catalyst such as $PtO_2$ and hydrogen gives the anomeric amine (XXXXI). Condensation of (XXXXI) with the carboxylic acid having Formula (XXXXII) gives the intermediate (XXXXIII). Debenzylation under a hydrogen atmosphere with a hydrogenation catalyst such as palladium on carbon gives the primary amine (XXXXIV). Condensation of the amine having Formula (XXXXIV) with the mitomycin A derivative (XII) gives the target derivative (XXXXV).

Scheme VII

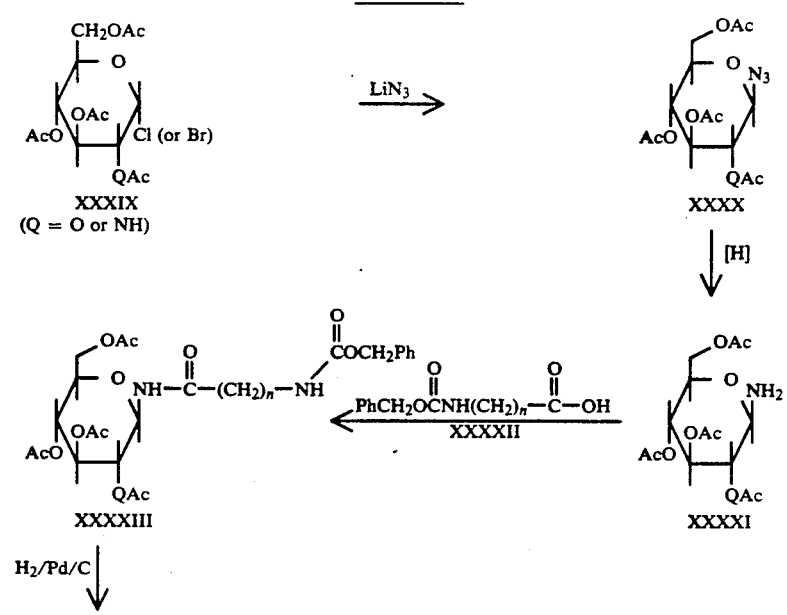

Scheme VII

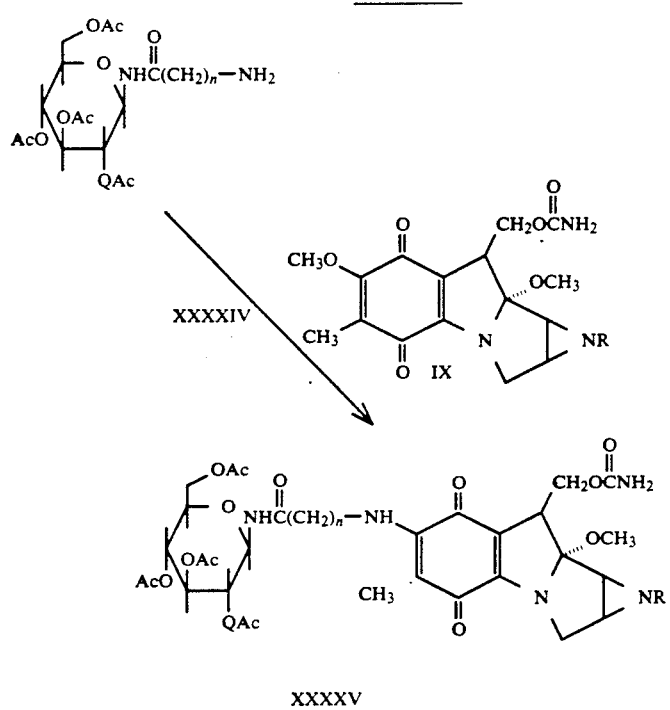

Other mitomycin derivatives of Formula VII may be produced as shown in Scheme VIII. The 1-thio saccharide (XXXXVI) is reacted with the dithioamine (XXXXVII) to give the primary amine (XXXXVIII). The compound having Formula (XXXXVIII) is then further reacted with the mitomycin A derivative (XII) to give mitomycin derivative (XXXXIX).

Scheme VIII

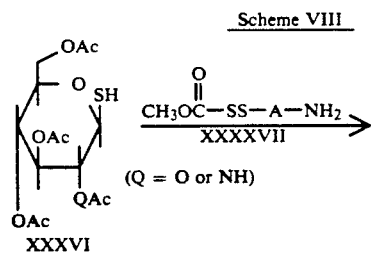

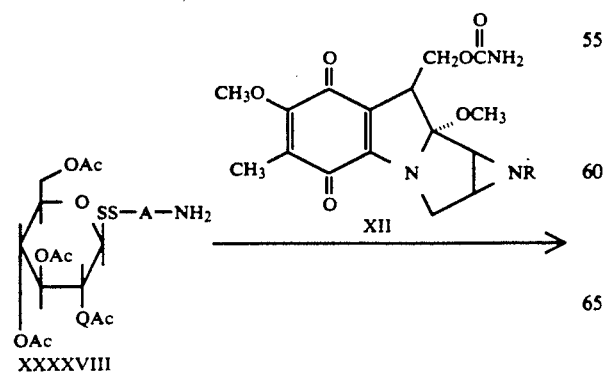

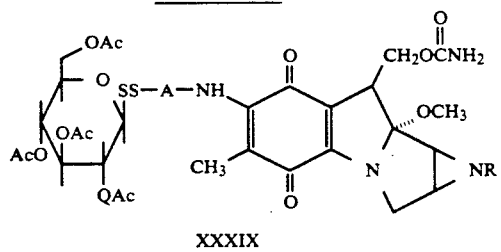

Mitomycin derivatives having Formula (VIII) may be prepared, for example, by treatment of the mitomycin A derivative (XII) with an amino compound having Formula (L) in a polar organic solvent as shown in Scheme IX.

Preferred mitomycin derivatives having Formula (VIII) include $N^7$-(4-phosphatophenyl)mitomycin C.

Scheme IX

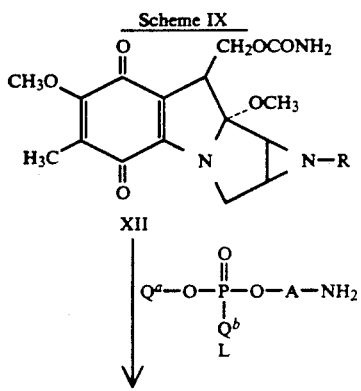

-continued
Scheme IX

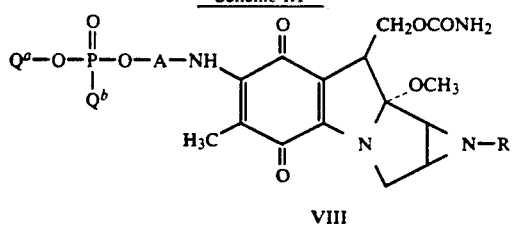

VIII

Mitomycin derivatives having Formula (X) may be prepared, for example, by treatment of the mitomycin A derivative (XII) with an amino compound having Formula (LI) in a polar organic solvent as shown in Scheme X.

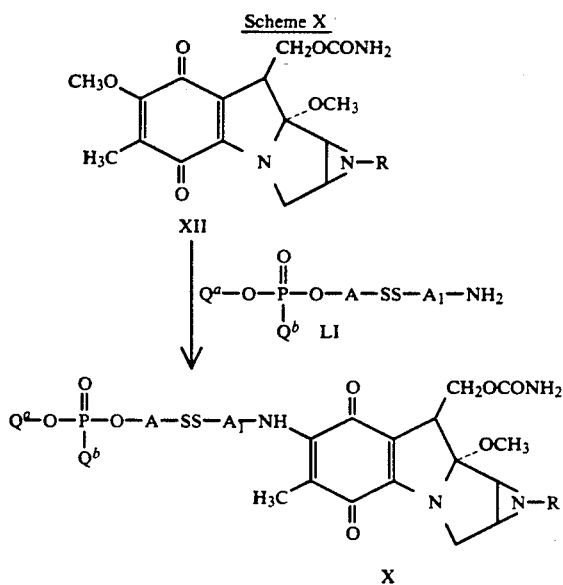

Typical $C_1$-$C_4$ alkyl groups include methyl, ethyl, n-propyl, i-propyl, n-butyl, t-butyl, and i-butyl groups.

Typical heteroaryl groups include furyl, thienyl, pyrrolyl, thiazolyl, pyridyl, pyrimidinyl, pyrizinyl and oxazolyl groups which may be fused to a benzene ring.

Typical substituted heteroaryl groups include the above-listed heteroaryl groups substituted by halo, $C_1$-$C_6$ alkyl and the like.

Typical $C_5$-$C_6$ heterocycloalkyl groups include tetrahydrofuranyl, tetrahydropyranyl, piperidinyl, morpholino and pyrrolidinyl groups.

The compounds of the invention may be present as pharmaceutically acceptable salts. Among the preferred anionic counter ions are those of the halides (derived from hydrohalic acids), such as chloride, bromide, or fluoride. Other anions include sulfonate, or p-toluenesulfonate.

As an antibiotic, the compounds of the present invention are useful against all microorganisms susceptible to the antibacterial action of the parent compounds, these microorganisms including, but not limited to, Pseudomonas, Staphylococcus, Sarcinia, Diplococcus, Streptococcus, Corynebacterium, Hemophilus, Escherichia, Klebsiella, Proteus, Salmonella, Shigella, Brucella, Mycobacterium, Nocardia, Saccharomyces, Candida, Penicillium, and Aspergillus. Specific microorganisms treatable with the compounds of the present invention include Pseudomonas aeruginosa, Staphylococcus aureus, Staphylococcus albus, Staphylococcus citreus, Sarcina lutea, Diplococcus pneumoniae, Streptococcus hemolyticus, Streptococcus lactis, Corynebacterium diphtheriae, Hemophilus pertussis, Escherichia coli, Klebsiella pneumoniae, Proteus vulgaris, Salmonella typhosa, Salmonella paratyphi, Shigella dysenteriae, Brucella abortus, Brucella megatherium, Brucella mycoides, Brucella anthracius, Mycobacterium ATCC 607, Mycobacterium avium, Mycobacterium phlei, Nocardia asteroides, Saccharomyces cervisiae, Candida albicans, Penicillium glacum, and Aspergillus niger.

The mitomycin derivatives of the present invention are useful in vitro as antiseptics, i.e. for disinfecting. The compounds are also useful topically and internally as therapeutic agents in combating pathogenic bacteria, e.g. in cases of staphylodermatitis, bacterial pneumoniae, leptopserosis, rickettsiosis, salmonellosis, and the like.

Typically, for topical application, the mitomycins of this invention are applied in compositions having concentrations in the range of 0.01 to 1000 ug/ml.

As antineoplastic agents, the compounds of the present invention are useful in treating a variety of cancers, including, but not limited to, those cancers susceptible to cell growth suppression by the parent compounds. Treatment of cancers with the parent compounds are described in the following references:

Driscoll, J. S. et al., Cancer Chemotherapy Rep. 4:1 (1974).

Kojima, R., et al., Cancer Chemotherapy Rep. 3:111 (1972).

Sugiura, K., Cancer Res. 19:438 (1959).

Oboshi, S., et al., Gann 58:315 (1967).

Sugiura, K., Cancer Chemotherapy Rep. 13:51 (1961).

Venditti, J. M., et al., Advances in Cancer Chemotherapy, pp. 201-209 (1978) Editors: H. Umezawa et al., Japan Soc. Press, Tokyo/Univ. Park Press, Baltimore.

Usubuchi, I., et al., Gann 58:307 (1967).

Typical cancers treated by the mitomycin derivatives of this invention include, but are not limited to gastric and pancreatic neoplasms (Schein, P. S. et al., in Mitomycin C: Current Status and New Developments, pp. 133-143, Carter et al. Eds., Academic Press, New York (1979)). Other cancers that may be treated using the compounds of the invention include lung, breast, anal, colorectal, head and neck, and melanoma.

The compounds of the invention are also active against the following tumor systems: Leukemia L-1210, Leukemia P388, P1534 leukemia, Friend Virus Leukemia, Leukemia L4946, Mecca lymphosarcoma, Gardner lymphosarcoma, Ridgway Osteogenic sarcoma, Sarcoma 180 (ascites), Wagner osteogenic sarcoma, Sarcoma T241, Lewis lung carcinoma, Carcinoma 755, CD8F, Mammary Carcinoma, Colon 38, Carcinoma 1025, Ehrlich carcinoma (ascites & solid), Krubs 2 carcinoma (ascites), Bashford carcinoma 63, Adenocarcinoma E 0771, B16 Melanoma, Hardin-Passey melanoma, Giloma 26, Miyona adenocarcinoma, Walker carcinosarcoma 256, Flexner-Jobling carcinoma, Jensen sarcoma, Iglesias sarcoma, Iglesias ovarian tumor, Murphy-Sturn lymphosarcoma, Yoshida sarcoma, Dunning leukemia, Rous chicken sarcoma, and Crabb hamster sarcoma.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the mitomycin derivative is contained in an amount effective to achieve its intended purpose. While individual needs vary, determination of optimal ranges of effective amounts of each component is with the skill of the art. Typical dosage forms contain 10 to 300 μmole/kg animal of the mitomycin derivative, or an equivalent amount of the pharmaceutically acceptable salt thereof.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 25 to 75 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

EXAMPLE 1: Preparation of Mitomycin A

Mitomycin C (50 mg, 0.15 mmol) was dissolved in 3 ml of a solution of 50% methanol and 50% 0.1N NaOH and stirred at room temperature for 18 hrs. After completion of the reaction (TLC, CHCl$_3$:MeOH, 10:1), the reaction mixture was quenched with dry ice to neutralize sodium hydroxide. The mixture was then freeze-dried in vacuo, and the mitosane compound was removed with methanol. The methanol solution was concentrated in vacuo to dryness, and the residue was redissolved in a minimum amount of methanol and then precipitated with ether to give 20 mg of a red-purplish powder. This was dissolved in 15 ml of ethyl acetate and cooled to 5° C., treated with diazomethane (etherial solution of diazomethane was prepared according to the procedure of Arndt, *Org. Synthesis*, Collective Volume II, pp. 165–167), and stirred for 20 minutes (TLC, CHCl$_3$:MeOH, 10:1). After completion of the reaction, the solvent was first removed under water aspirator reduced pressure and then dried in vacuo. The residue was recrystallized from ether to give 18 mg of reddish needles, m.p. 159°–160° C. TLC (EtOAc:acetone, 1:1) gave one spot $R_f=0.91$, and (acetone:benzene, 4:1) one spot $R_f=0.48$. UV (methanol) 216 and 358 mu. NMR (acetone-d$_6$, middle peak of acetone at 2.10), δ, 5.94 (br, 2H); 4.76 (dd, 1H); 4.38 (t, 1H); 4.07 (s, 3H); 3.96 (d, 1H); 3.54 (dd, 1H); 3.41 (d, 1H); 3.35 (d, 1H); 3.25 (s, 3H); 2.99–2.264 (mmm); 2.87 (s); 1.640 (s, 3H).

EXAMPLE 2: Preparation of N$^7$-(2-deoxyglucopyranosyl)mitomycin C

To a solution of mitomycin A (10 mg, 0.028 mmol) in absolute methanol was added a methanolic solution of glucosamine.HCl (70 mg, 0.325 mmol) and diisopropylethylamine (100 ul). This mixture was stirred under N$_2$ atmosphere at room temperature until the reaction was complete by TLC (EtOAc:acetone, 1:1), at which time (10 hrs.) the solution had changed color from reddish to dark purple. The solution was concentrated by evaporation with a N$_2$ stream and chromatographed on a preparative silica plate eluted with acetone-ethyl acetate (1:1). The purple band remaining close to the origin was scraped off and eluted with methanol. Further purification by HPLC (C$_{18}$ reversed phase, semi-preparative column, methanol: 0.1N phosphate buffer, 1:1) gave a purple powder, NMR (D$_2$O) δ5.32 (d, 1H, saccharide anomeric H); 3.85 (s, 3H, 9a-OCH$_3$); and the disappearance of singlet at 4.09 (Matsui, M., et al., *J. Antibiot.* 21:189 (1968); Cheng, L., and Remers, W. A., *J. Med. Chem.* 20:767 (1977); Vyas, D. M., et al., *J. Org. Chem.* 51:4307 (1986)).

EXAMPLE 3: Preparation of N-(2,6-Dihydroxycyclohexyl)glycinamide

To a solution of N-benzyloxycarbonylglycine (3 g, 14.3 mmol) in dioxane was added N-hydroxysuccinimide (1.65 g, 14.3 mmol) and N,N-dicyclohexylcarbodiimide (2.96 g, 14.3 mmol) with cooling. The reaction mixture was stirred at 0°–5° C. for one hour and allowed to stand under refrigeration overnight. The urea precipitate was removed by suction filtration and the filtrate was concentrated in vacuo to dryness. The yellowish residue was recrystallized from ethyl acetate-ether to give an 84% yield of the glycine activated ester mp. 112°–114° C. NMR (CHCl$_3$).

The above-prepared activated ester of glycine (25 g, 0.008 mol) was dissolved in 15 ml of dry DMF (dimethyl formamide), chilled to below 5° C., and 2-amino-1,3-cyclohexanediol (2.18 g, 0.016 mol) in DMF was added drop-wise with stirring under N$_2$ atmosphere. After completion of the reaction (TLC, CHCl$_3$:MeOH, 10:1), DMF was removed under reduced pressure and the resulting solid residue was crystallized from ethyl acetate to give white crystals in 84% yield, m.p. 170°–172° C. NMR (D$_2$O): δ7.45 (s, 5H, aromatic H); 5.20 (s, 2H, benzylic-CH$_2$); 3.95 (s, 2H, —CO—CH$_2$—NH$_2$); 3.6 (t, 1H, C$_1$H of cyclohexane ring); 3.45 (m, 2H, C$_2$H and C$_6$H of cyclohexane ring); 2.0, 1.8 and 1.35 (m,m,m, 2 to 1 to 3H; C$_3$, C$_4$ and C$_5$ hydrogens of cyclohexane). The product comprises the N-protected benzyloxycarbonyl derivative of N-(2,6-dihydroxycyclohexyl)glycinamide.

N-protected benzyloxycarbonyl N-(2,6-dihydroxycyclohexyl) glycinamide (3 g, 0.093 mol) was dissolved in 100 ml of absolute ethanol with a molar equivalent of 10% HCl. Hydrogenolysis with 5% Pd/C at 30 psi, removal of the catalyst over celite, and subsequent evaporation of solvents in vacuo yielded a pale brownish solid which was triturated with ether and recrystallized from ethyl acetate and ether, m.p. 207°–210° C. NMR (D$_2$O), δ, 3.65 (t, 3H, C$_1$H of cyclohexane ring); 3.55 (m, 2H, C$_2$H and C$_6$H of cyclohexane); 3.4 (s, 2H, —CO—CH$_2$—NH$_2$); 2.05, 1.80, and 1.38 (m,m,m, 2 to 1 to 3H, hydrogens of C$_3$, C$_4$ and C$_5$ of cyclohexane).

EXAMPLE 4: Preparation of 7-{3-[(2-acetamido-3,4,6-tri-O-acetyl-β-D-glucopyranosyl)-amino]carbonylpropylamino}-9-methoxymitosane (MC 62)

2-Acetamido-3,4,6-tri-O-acetyl-2-deoxy-α-D-glucopyranosyl chloride was prepared as follows. 2-Acetamido-2-deoxy-D-glucose (50 g, 0.226 mol) was added to chilled acetyl chloride (125 ml). The mixture was then stirred at room temperature for 16 hr. Chloroform (300 ml) was added to the reaction mixture through the condenser and the resulting homogeneous solution was added to a vigorously stirred solution of 400 grams of ice and 100 ml of water. The organic layer was separated, washed with saturated sodium bicarbonate, dried over anhydrous sodium sulfate, and filtered. This filtrate was concentrated to about 75 ml under reduced pressure. Ether (400 ml) was added to the concentrated solution and left at room temperature for 2 hr to give the product as a white solid. This white solid was filtered and dried in a vacuum desiccator over sodium hydroxide and phosphorous pentoxide to give 52.5 grams of the title cmp. M.p. 123°–125° C.

2-Acetamido-3,4,6-tri-O-acetyl-2-deoxy-β-D-glucopyranosylamine was prepared as follows. 2-Acetamido-3,4,6-tri-O-acetyl-2-deoxy-α-D-glucopyranosyl bromide (11.25 g, 30.8 mmol) was reacted with lithium azide (2.25 g, 46 mmol) in refluxing acetone (50 ml) under nitrogen atmosphere for 19 hr. The acetone was then removed under reduced pressure to give a semi-solid residue, which was taken up in a mixture of chloroform and water. The organic layer was separated, dried over anhydrous sodium sulfate, and filtered. The filtrate was evaporated to dryness to give the crude azo-saccharide as a brownish residue. This residue was dissolved in ethyl acetate and decolorized with activated carbon. Addition of ether to the ethyl acetate containing the product yielded the sugar azide as a white precipitate. TLC on silica (methanol:chloroform/1:9) showed a single homogenous spot. The resulting azide (4.0 g) was hydrogenated over platinum oxide (0.3 g) at room temperature and atmospheric pressure. After the completion of the reaction, the catalyst was filtered off and the solution was evaporated to dryness to give the aminosaccharide (3.4 g) as a white solid. TLC gave one spot (methanol:chloroform/1:9).

N-(2-Acetamido-3,4,6-tri-O-acetyl-2-deoxy-β-D-glucopyranosyl)-4-(benzyloxycarbonyl)aminobutanamide was prepared as follows. The amino saccharide obtained above (3.796 g, 10.97 mmol) was reacted with 4-(benzyloxycarbonyl)aminobutyric acid (2.60 g, 10.97 mmol) in THF (100 ml) in the presence of EEDQ (2-ethoxy-1-ethoxycarbonyl-1,2-dihydroquinoline (2.894 g, 11.7 mmol) for 6 days at 32° C. The reaction mixture was evaporated to give a pale yellow solid which was suspended in a mixture of ethyl acetate and ether. The solid was then filtered and washed with 1.0M HCl, water, 5% NaHCO$_3$, water, and dried under vacuum to give the product as a white powder. M.p. 206°–207° C. Analytical calc. for C$_{26}$H$_{35}$N$_3$O$_{11}$: C(55.22), H(6.24), N(7.43). Found: C(55.58),H(6.29), N(7.35).

N-(2-Acetamido-3,4,6-tri-O-acetyl-2-deoxy-β-D-glucopyranosyl)-4-aminobutanamide was prepared as follows. The benzyloxycarbonyl derivative obtained above (1.5 g) in ethanol (250 ml) was hydrogenated over 10% palladium on carbon (0.8 g) at room temperature. After the completion of the reaction, the catalyst was removed and the solution was evaporated to dryness under reduced pressure yielding the amine (0.23 g). Analytical calc. for $C_{18}H_{29}N_3O_9$: C(50.11), H(6.78), N(9.74). Found: C(50.57), H(7.17), N(8.72).

7-{3-[(2-acetamido-3,4,6-tri-O-acetyl-β-D-glucopyranosyl)-amino]carbonylpropylamino}-9-methoxymitosane (MC-62) was prepared as follows. To a solution of mitomycin A (31 mg) in anhydrous methanol (2 ml) was added 2-N-(2-acetamido-3,4,6-tri-O-acetyl-2-deoxy-β-D-glucopyranosyl)-4-aminobutanamide (150 mg). The mixture was stirred in the dark at room temperature under a nitrogen atmosphere until TLC (chloroform:methanol/9:1) showed completion. The solvent was removed under reduced pressure and the crude product chromatographed on a silica gel preparative plate (20×20, 1 mm thickness) with methanol:-chloroform (1:9) as eluent. Removal of the solvent gave 41 mg of the title compound. TLC revealed a single spot (methanol:methylene chloride/1:9, Rf=0.31).

EXAMPLE 5: Preparation of 7-{2-[(2-acetamido-3,4,6-tri-O-acetyl-β-D-glucopyranosyl)amino]carbonylethylamino}-9-methoxymitosane 7-{2-[(2-acetamido-3,4,6-tri-O-acetyl-β-D-glucopyranosyl)amino]carbonylethylamino}-9-methoxymitosane was prepared as described in Example 4 except that 2-N-(2-acet-amido-3,4,6-tri-O-acetyl-2-deoxy-β-D-glucopyranosyl)-3-aminopropanamide was used in place of 2-N-(2-acetamido-3,4,6-tri-O-acetyl-2-deoxy-β-D-glucopyranosyl)-4-aminobutanamide.

EXAMPLE 6: Preparation of 7-{[4-(2,3,4,6-tetra-O-acetyl-β-D-glucopyranosyl)oxyphenyl]amino}-9-methoxymitosane (MC-77)

7-{[4-(2,3,4,6-tetra-O-acetyl-β-D-glucopyranosyl)oxyphenyl]amino}-9-methoxymitosane (MC-77) was prepared as described in Example 4 except that 4-(2,3,4,6-tetra-O-acetyl-β-D-glucopyranosyl)oxyaniline was used in place of 2-N-(2-acetamido-3,4,6-tri-O-acetyl-2-deoxy-β-D-glucopyranosyl)-4-aminobutanamide. Analytical calc. for $C_{35}H_{40}N_4O_{15}$: C(55.56), H(5.33), N(7.40). Found: C(55.86), H(5.67), N(6.73).

4-aminophenyl-2,3,4,6-tetra-O-acetyl-β-D-glucopyranoside was produced by the following procedure. To a solution of 2,3,4,6-tetra-O-acetyl-α-D-glucopyranosyl bromide (10 g, 24 mmol) in chloroform (100 ml) was added a mixture of p-nitrophenol (6.67 g, 48 mmol), benzyltriethylammonium bromide (BTEAB, 5.53 g, 20 mmol) and 1.25N NaOH (50 ml, 62 mmol). After stirring at 60° C. for 3½ hr the solution was diluted with water (100 ml). The organic layer was separated, washed with 1.25N NaOH, water, and dried over anhydrous sodium sulfate. Removal of the solvent under reduced pressure gave a yellow powder. 4-Nitrophenyl-2,3,4,6-tetra-O-acetyl-β-D-glucopyranoside was crystallized from boiling 95% ethanol as a white precipitate (5.30 g). M.p. 178-179. This compound (16.44 g) was hydrogenated over 10% palladium on activated carbon at room temperature. The catalyst was filtered off and the solvent was completely evaporated to give 4-aminophenyl-2,3,4,6-tetra-O-acetyl-β-D-glucopyranoside (5.82 g) as a white powder.

EXAMPLE 7: Preparation of 7-{[4-(2,3,4,6-tetra-O-acetyl-β-D-glucopyranosyl)dithio]ethylamino}-9-methoxymitosane 7-{[4-(2,3,4,6-Tetra-O-acetyl-β-D-glucopyranosyl)-dithio]ethylamino}-9-methoxymitosane was prepared as described for in Example 6 except that 4-(2,3,4,6-tetra-O-acetyl-β-D-glucopyranosyl)dithioethylamine.HCl was used instead of 2-N-(2-acetamido-3,4,6-tri-O-acetyl-2-deoxy-β-D-glucopyranosyl)-4-aminobutanamide. TLC showed a single spot (chloroform:methanol/9:1, Rf=0.43).

2,3,4,6-Tetra-O-acetyl-β-D-glucopyranosyl)dithioethylamine.HCl was prepared as follows. To a stirred solution of methyl-2-aminoethylsulfenylthiocarbonate.HCl (447 mg, 2.196 mmol) in methanol (5 ml) was added 2,3,4,6-tetra-O-acetyl-1-thio-β-D-glucose (800 mg, 2.196 mmol) in methanol (10 ml). After stirring at room temperature overnight, the mixture was evaporated to dryness yielding the tetraacetate as a white solid.

EXAMPLE 8: Preparation of 7-{[4-(2-acetamido-3,4,6-tri-O-acetyl-β-D-glucopyranosyl)dithio]ethylamino}-9-methoxymitosane 7-{[4-(2-Acetamido-3,4,6-tri-O-acetyl-β-D-glucopyranosyl)dithio]ethylamino}-9-methoxymitosane was prepared as described in Example 7 except that 4-(2-acetamido-3,4,6-tri-O-acetyl-β-D-glucopyranosyl)dithioethylamine.HCl was used instead of 2-N-(2-acetamido-3,4,6-tri-O-acetyl-2-deoxy-β-D-glucopyranosyl)-4-aminobutanamide. TLC showed a single spot (chloroform: methanol/9:1; Rf=0.26).

4-(2-Acetamido-3,4,6-tri-O-acetyl-β-D-glucopyranosyl)dithioethylamine.HCl was prepared as follows. To a stirred solution of methyl-2-aminoethylsulfenylthiocarbonate HCl (447 mg, 2.196 mmol) in methanol (5 ml) was added 2-acetamido-3,4,6-tri-O-acetyl-1-thio-β-D-glucose (798 mg, 2.196 mmol) in methanol (10 ml). After stirring at room temperature over night, the mixture was evaporated to dryness yielding the triacetate as a white solid.

EXAMPLE 9: Preparation of 7-{[4-(2,3,4,6-tetra-O-acetyl-β-D-glucopyranosyl)dithio]phenylamino}-9-methoxymitosane 7-{[4-(2,3,4,6-tetra-O-acetyl-β-D-glucopyranosyl)dithio]phenylamino}-9-methoxymitosane was prepared as described in Example 7 except that 4-(2,3,4,6-tetra-O-acetyl-β-D-glucopyranosyl)dithioaniline.HCl was used in place of 2-N-(2-acetamido-3,4,6-tri-O-acetyl-2-deoxy-β-D-glucopyranosyl)-4-amino-butanamide. TLC showed a single spot (chloroform:methanol/9:1; Rf=0.43).

4-(2,3,4,6-Tetra-O-acetyl-β-D-glucopyranosyl)dithioanaline.HCl was prepared as follows. A solution of 2,3,4,6-tetra-O-acetyl-1-thio-β-D-glucose (591 mg, 1.07 mmol) in methanol (5 ml) was added dropwise to a solution of methyl-4-aminophenylsulfenylthiocarbonate HCl (270 mg, 1.07 mmol) in methanol (2 ml). After stirring at room temperature over night, the solvent was removed under reduced pressure to give 480 mg of the dithiosugar.

EXAMPLE 10: Preparation of N⁷-(4-phosphatophenyl)mitomycin C

Disodium-4-aminophenylphosphate. A mixture of 2.5 g disodium-4-nitrophenylphosphate (Aldrich), 2.0 g palladium on carbon, and 250 ml aqueous ethanol (50%) was hydrogenated at room temperature at 35 psi overnight. The catalyst was removed by filtration and the solution was concentrated under vacuum to about 5 ml. Dilution of this solution with absolute ethanol resulted in the precipitation of the product. The product was filtered and washed with ethanol, ether, and dried to give 1.455 g (92.7%) of disodium-4-aminophenylphosphate as an off-white powder.

N$_7$-(4-phosphatophenyl)mitomycin C was prepared according to Scheme IX. A mixture of 23.8 mg mitomycin A (prepared as previously described) and 24 mg of disodium-4-aminophenylphosphate in 1.0 ml dry methanol was stirred at room temperature for 5 hr. Methanol was removed under reduced pressure and the resulting greenish residue was taken up in water, washed with chloroform (3×5 ml), and freeze-dried to afford 34.6 mg N$^7$-(4-phosphatophenyl)mitomycin C.

EXAMPLE 11

Animal Studies

The compound N$^7$-(2-deoxyglucopyranosyl)mitomycin C, prepared according to Example 2, was evaluated for both murine P388 leukemia antitumor activity and toxicity to bone marrow in normal mice.

A. Determination of Murine Antitumor Activity

The murine P388 leukemia system, maintained intraperitoneally in female DBA/2 mice, was used to evaluate antitumor activity. This tumor was selected because of its known sensitivity to the parent compound, mitomycin C (Driscoll et al., *Cancer Chemotherapy Reports* 4: 1 (1974)). N$^7$-(2-deoxyglucopyranosyl)mitomycin C was dissolved in sterile water (at 4° C.) immediately prior to administration. Mitomycin C was dissolved in ethanol, and the resultant solution was adjusted to 5% ethanol, 95% sterile water.

Each compound was administered intraperitoneally to groups of CD2F$_1$ male mice on Day 1 after intraperitoneal implantation of 1×10⁶ P388 leukemia cells. The P388 antileukemic activity of the test compound was assessed by mean survival days and percentage increased life span (ILS). The % ILS was calculated as follows:

% ILS = (i T−C)/C × 100;

where T is the mean survival days of the treated mice and C is the mean survival days of the untreated mice.

P388 antitumor activity for N$^7$-(2-deoxyglucopyranosyl)mitomycin C, in comparison with the parent mitomycin C, is summarized in Table 2:

TABLE 2

| Antitumor Activity Against P388 Leukemia | | | |
|---|---|---|---|
| Drug (days) | Dose (mg/kg) | % ILS | Mean Survival |
| N$^7$-(2-deoxyglucopyranosyl)mitomycin C | 5$^a$ | 42% | 14.2 |
|  | 13.5$^a$ | 61% | 16.1 |
| Mitomycin C | 4.5$^b$ | 81% | 18.1 |

TABLE 2-continued

| Antitumor Activity Against P388 Leukemia | | | |
|---|---|---|---|
| Drug (days) | Dose (mg/kg) | % ILS | Mean Survival |
| Control$^c$ |  |  | 10.0 |

$^a$LD$_0$ dose
$^b$Approximate LD$_{10}$ dose
$^c$Treated with drug vehicle

B. Determination of the effects of N$^7$-(2-deoxyglucopyranosyl)mitomycin C on the hematopoietic system in mice Measurement of peripheral leukocyte (WBC) count was performed using a 20-ul sample of retro-orbital sinus blood obtained from normal CD2F$_1$ male mice on Day 3 following i.p. administration of 13.5 mg/kg of N$^7$-(2-deoxyglucopyranosyl)mitomycin C or 4.5 mg/kg of mitomycin C. Blood samples obtained were diluted in 9.98 ml of Isoton (a neutral, isotonic buffer solution) and counted in a Coulter counter after lysis with Zapoglobin (an enzyme solution which lyses red blood cells, but not white blood cells). WBC counts are expressed as a percentage of values from control mice receiving drug vehicle only. The results are summarized in the following table:

TABLE 3

| In vivo Murine WBC Depression | | |
|---|---|---|
| Drug | Dose | WBC Count on Day 3 (as percent of control) |
| N$^7$-(deoxyglucopyranosyl)mitomycin C | 13.5 mg/kg | 94% |
| Mitomycin C | 4.5 mg/kg | 56–66% |

In summary, these in vivo studies demonstrate that N$^7$-(2-deoxyglucopyranosyl)mitomycin C has significant activity against the murine P388 tumor system, at doses producing no significant bone marrow toxicity, as determined by depression of peripheral leukocyte (WBC) count.

EXAMPLE 12: Antibacterial Activity

N$^7$-(2-deoxyglucopyranosyl)mitomycin C was evaluated for activity against Gram-negative bacteria, in a comparative study with the parent mitomycin C. Minimum inhibition concentration (M.I.C.) against a Gram-negative strain of bacteria (HB101) was estimated by the dilution method, with graded concentrations of drug added to agar at 37°–40° C. N$^7$-(2-deoxyglucopyranosyl)mitomycin C was dissolved in 50% sterile water-50% ethanol at 4° C., and mitomycin C was dissolved in ethanol. The agar, containing drug, quickly solidified at room temperature, and the bacteria were plated immediately. After 24 hours at 37° C., the agar plates were observed for inhibition of bacterial growth. The results are summarized in Table 4.

TABLE 4

| Compound | M.I.C. Gram-negative Bacteria |
|---|---|
| N$^7$-(2-deoxyglucopyranosyl)mitomycin C | 1.66–3.3 mcg/ml |
| Mitomycin C | 0.3–0.5 mcg/ml |

EXAMPLE 13: Testing in vitro

Mitomycin-C induces a significant percentage of objective responses in patients with metastatic breast cancer. Since a major use of analogues would be for the treatment of this disease, in vitro screening against human breast cancer cell lines was investigated. Two cell lines were investigated. The MDA-MB-231 cell line is representative of tumors which have no detectable estrogen receptors, do not require estrogen for tumor formation in a thymic nude mice, are resistant to antiestrogen therapy and have a poor prognosis. The MCF-7 cell line retains estrogen receptor expression, has an absolute requirement for estrogen to form tumors in nude mice, responds to antiestrogen therapy and is more representative of tumors with a better prognosis.

(a) Inhibition of DNA Synthesis

Figure 2:
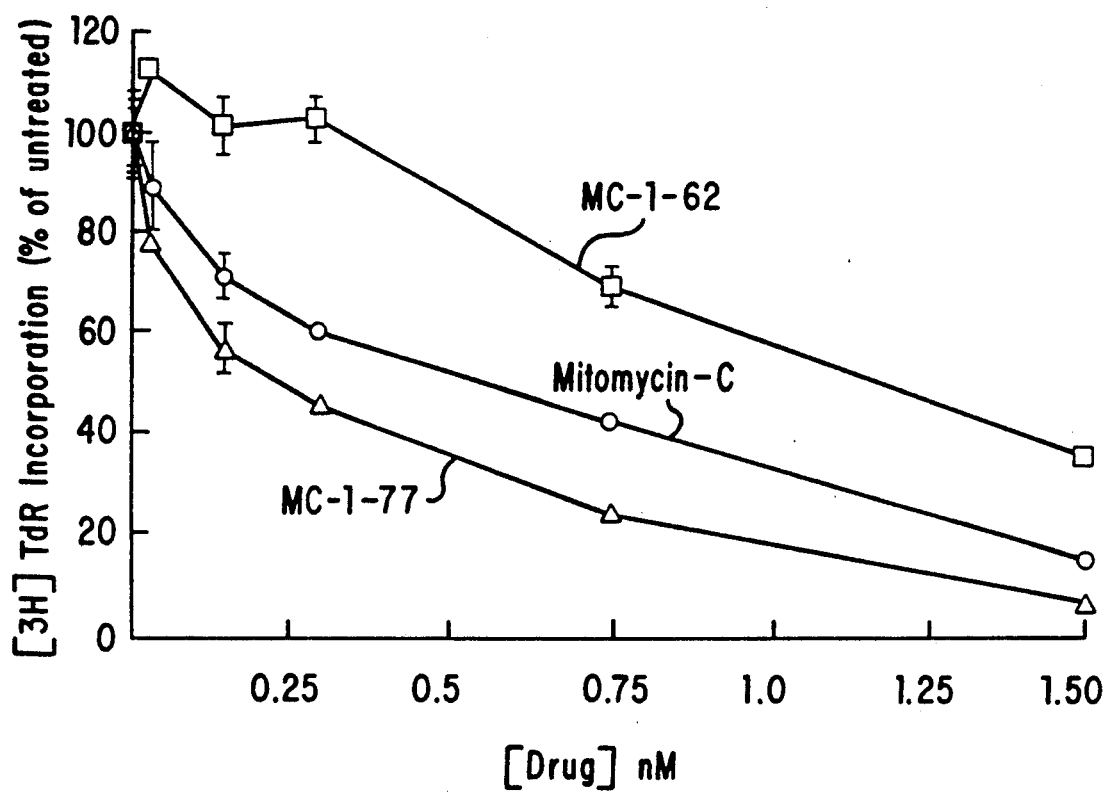
FIG. 2 depicts a graph showing the response of the MCF-7 human breast tumor cell line to several concentrations of the drugs mitomycin-C, MC-1-77, and MC-1-62.

The cytotoxic effects of Mitomycin-C are largely the result of its interactions with DNA. Consequently, the ability of Mitomycin-C and its analogues to inhibit the rate of incorporation of [$^3$H] deoxythymidine into DNA was initially determined. Deoxythymidine is an essential precursor for the synthesis of DNA. The experiments were performed as described by Clarke et al., *Br. J. Cancer* 51: 365–369 (1985). Pharmacologically relevant concentrations of Mitomycin-C and MC-77 induce a significant and dose dependent inhibition of DNA synthesis in both MDA-MB-231 (FIG. 1) and MCF-7 human breast tumor cells (FIG. 2). At equimolar concentrations, a two to five fold greater inhibition of DNA synthesis was observed following treatment with MC-77 when compared with the parent compound. In marked contrast, MC-62 is significantly less potent than both Mitomycin-C and MC-77.

(b) Inhibition of the Rate of Cell Proliferation

Figure 3A:
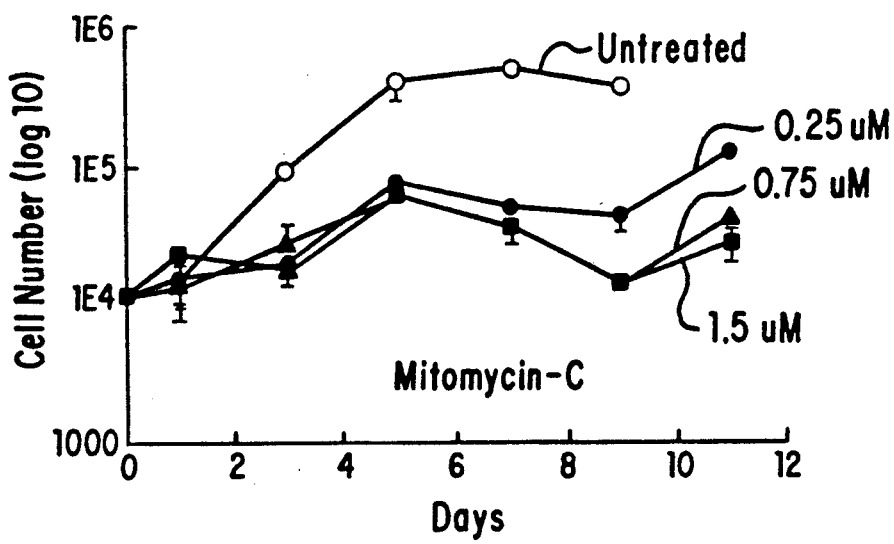
FIGS. 3A-3C depicts three graphs showing the effect of Mitomycin-C, MC-77 and MC-62 on the cell population kinetics of MDA-MB-231 cells. Both Mitomycin-C and MC-77 significantly inhibited the rate of cell proliferation.
Figure 3B:
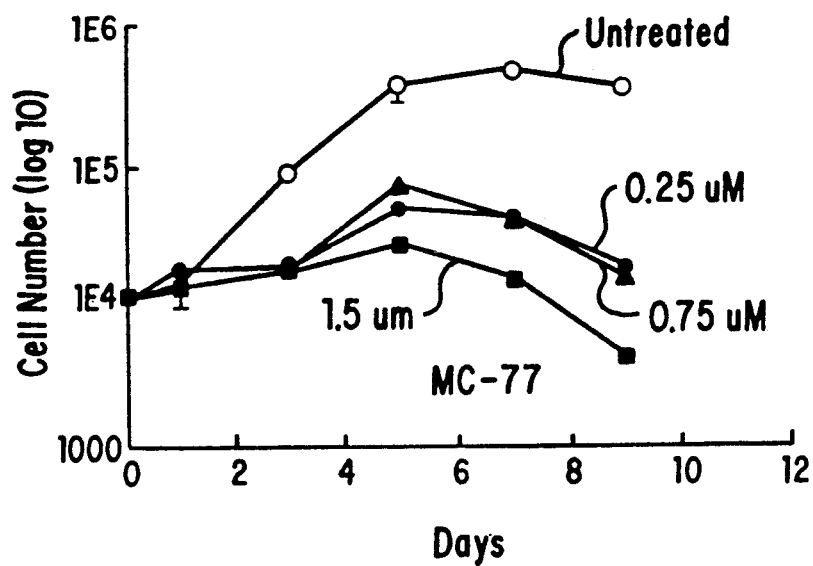
Figure 3C:
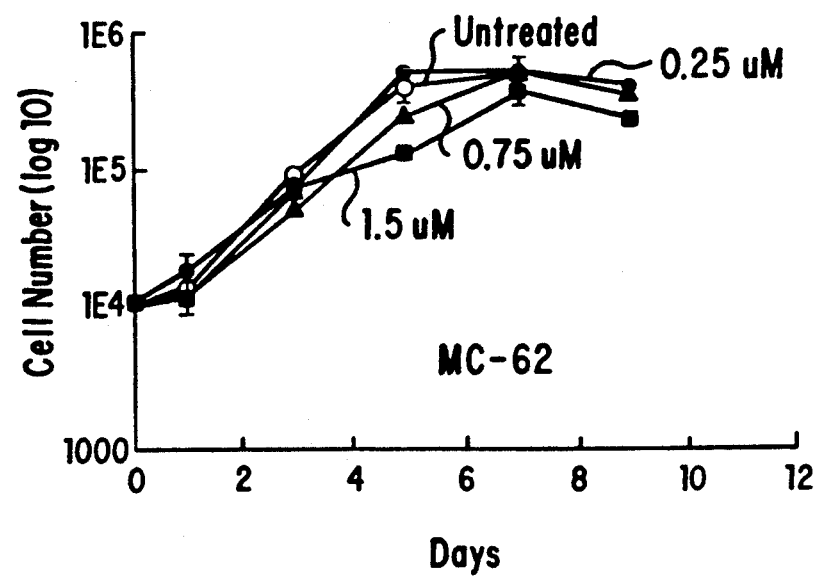

The interpretation of the effects of cytotoxic drugs on the rate of cell proliferation is a more difficult endpoint to interpret. For example, a cytotoxic agent may apparently reduce the rate of cell growth by killing a proportion of the cells. Alternatively, all the cells in the population may be growth arrested but not killed. Both of these series of events could produce identical growth curves. However, cell killing is clearly evidenced when the cell number falls significantly below the starting cell number (van den Berg et al., *Eur. J. Cancer Oncol.* 17: 1275–1281 (1981)). FIG. 3 shows the effect of Mitomycin-C, MC-77 and MC-62 on the cell population kinetics of MDA-MB-231 cells. MC-62 failed to markedly influence the rate of MDA-MB-231 growth. Both Mitomycin-C and MC-77 significantly inhibited the rate of cell proliferation. However, only treatment with 1.5 uM MC-77 reduced cell number below starting cell number.

(c) Anchorage-dependent Colony Formation

Figure 4:
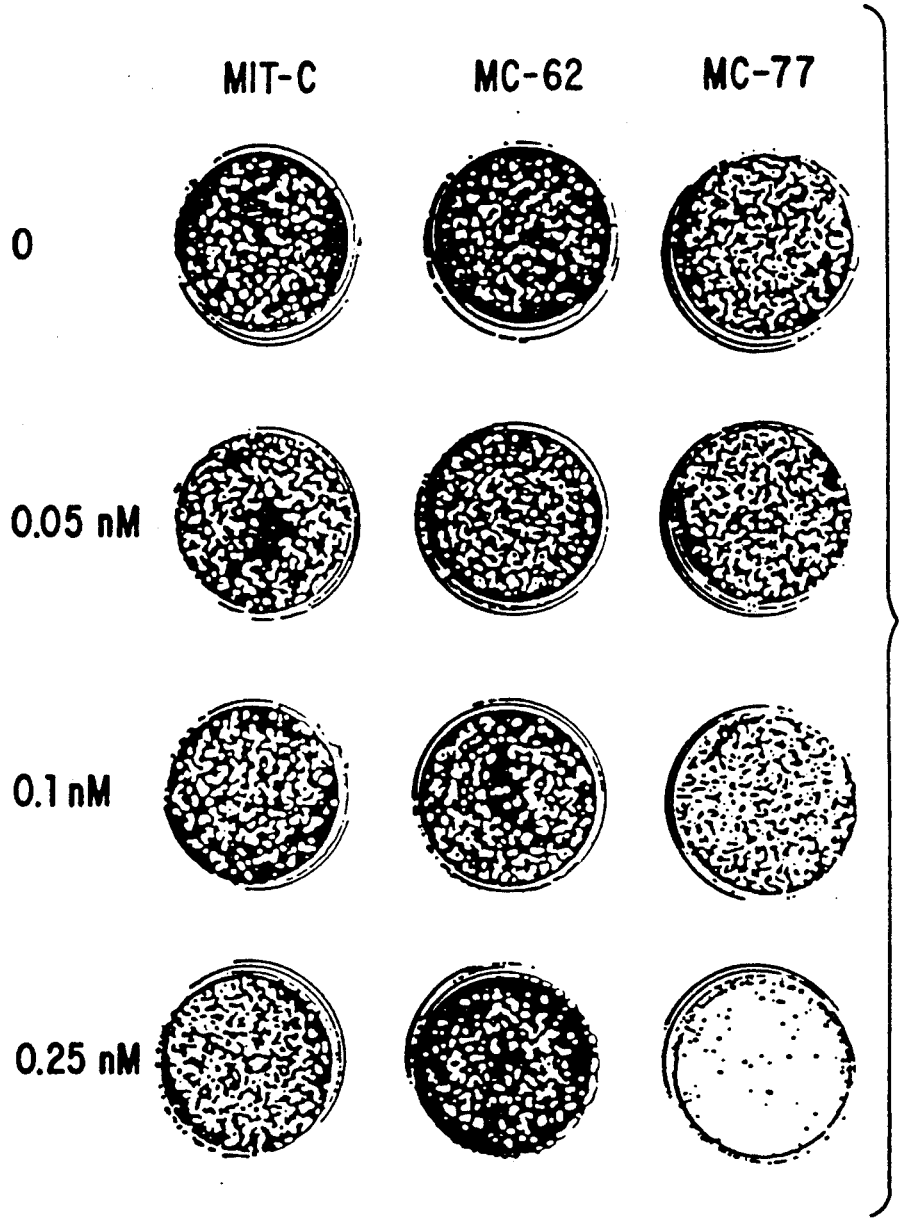
FIG. 4 shows the effect of several concentrations of Mitomycin-C, MC-77 and MC-62 on the anchorage-dependent colony forming ability of MDA-MB-231 cells.

Many cytotoxic drugs do not kill cells until they and their progency have completed one or more cell divisions. Consequently, the most accurate methods for determining cell kill measure the ability of a single cell to produce a clone of 50 or more cells (equivalent to six or more divisions). Two clonogenic assays were utilized. The anchorage-dependent assay provides the cells with a solid plastic substrate for attachment. The experiments were preformed as described by van den Berg et al. (1981), supra. FIG. 4 shows the effect of Mitomycin-C, MC-77 and MC-62 on the anchorage-dependent colony forming ability to fMDA-MB-231 cells. Treatment with MC-62 did not significantly influence colony formation. Both MC-77 and the parent compound induced a significant reduction in colony forming ability following treatment with 0.25 uM drug. The inhibition induced by 0.25 uM MC-77 is estimated to be approximately two to five fold greater than that induced by an equimolar concentration of Mitomycin-C.

(d) Anchorage-Independent Colony Formation

Figure 5A:
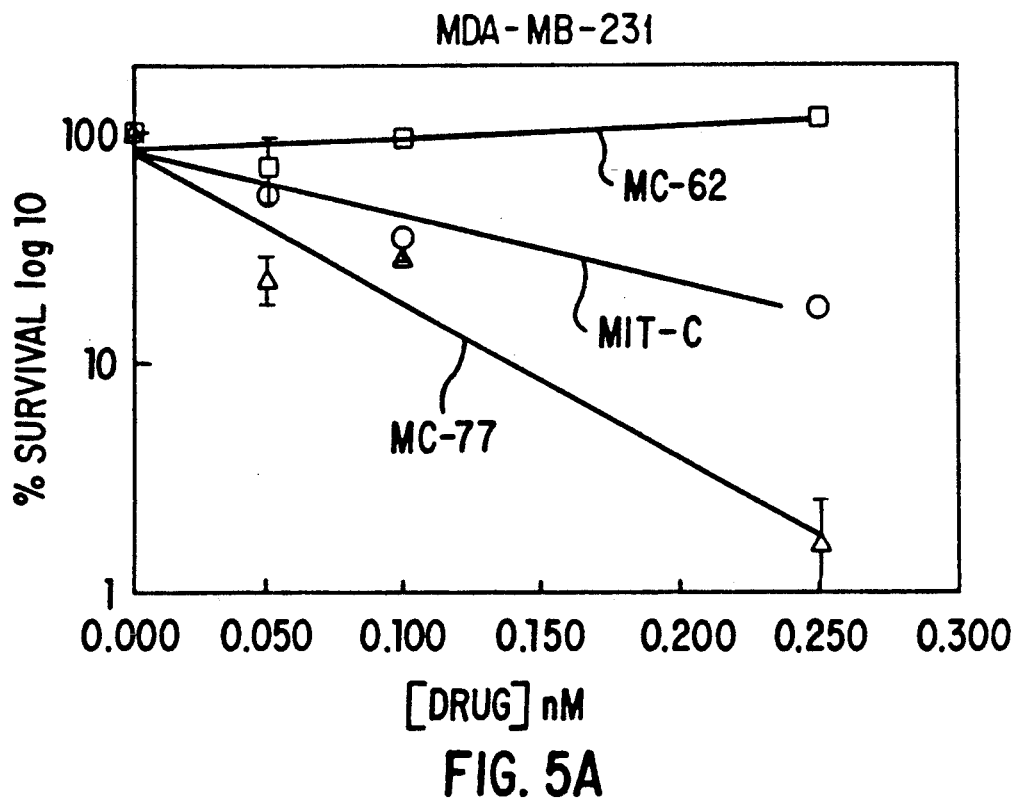
FIGS. 5A-5B depicts two graphs showing the results of two anchorage-independent colony formation assays.
Figure 5B:
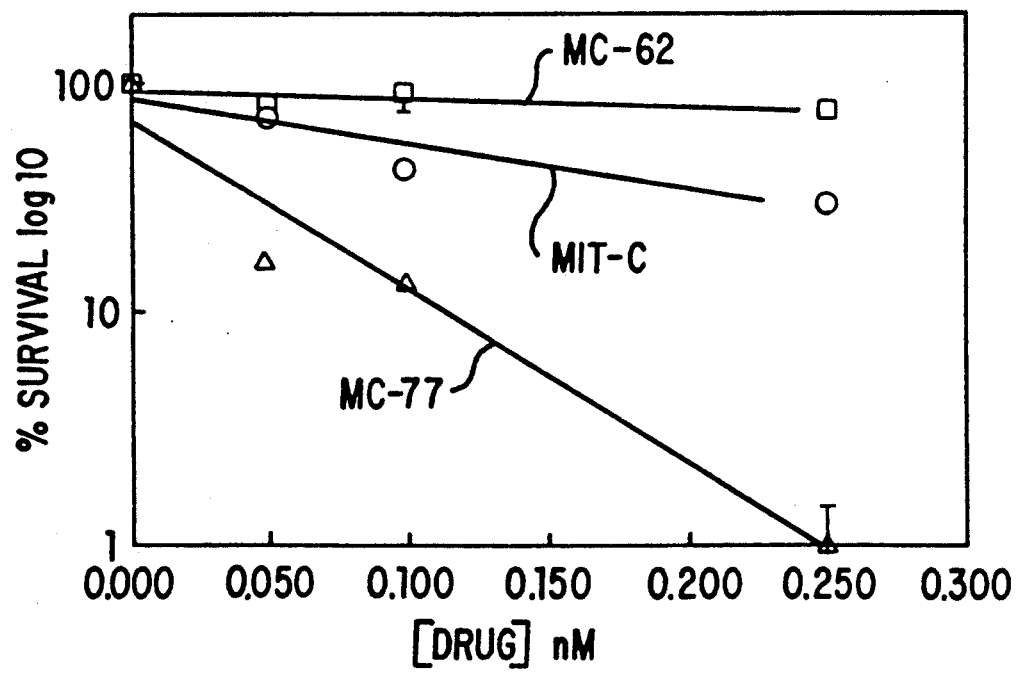

The anchorage-independent assay ensures that the cells grow in suspension in a soft agar solution. Thus, cells must retain both their basal reproductive integrity and their ability to grow in suspension. The data in FIG. 5 represents the results of two anchorage-independent colony formation assays. The assays were performed as described by Clarke et al., *J. Endocrinol.* 122: 331–340 (1989). MC-62 consistently fails to influence colony formation. Both Mitomycin-C and MC-77 induce dose dependent reductions in cell survival. However, MC-77 appears to be two to five fold more cytotoxic when compared with Mitomycin-C.

(e) Conclusions

The data from all four endpoints clearly indicate that the structural modifications present in MC-62 have significantly reduced antineoplastic potential. However, a shift in the dose response curve of MC-77 compared with the parent drug is consistently observed, clearly indicating a marked improvement in the cytotoxic potential of between two and five fold.

EXAMPLE 14: Testing in vivo: Murine P388 Leukemia Antitumor Activity $N^7$-(4-phosphatophenyl)mitomycin C was evaluted for murine P388 antitumor activity in comparative studies with the parent mitomycin C. P388 leukemia, maintained intraperitoneally in female DBA/2F$_1$ mice, was selected because of its known sensitivity to mitomycin C (Driscoll et al., *Cancer Chemotherapy Report* 4: 1 (1974)). The optimal single ip P388 therapeutic dose of mitomycin C is 4.5–5.5 mg/kg.

Each compound was administered intraperitoneally to groups of CD2F$_1$ male mice on Day 1 following intraperitoneal implantation of $1 \times 10^6$ P388 leukemia cells. In these comparative studies with the parent mitomycin C, the P388 antileukemic activity of $N^7$-(4-phosphatophenyl)mitomycin C, administered at a range of doses, was assessed by calculation of percentage increase of life span, where $$\% \text{ ILS} = (T-C)/C \times 100$$

and

T is the mean survival days of mice receiving drug=-treated mice

C is the mean survival days of the mice receiving drug vehicle.

Weight loss resultant from drug toxicity was also determined.

TABLE 5

| Drug | P388 Leukemia Antitumor Activity | |
|---|---|---|
| | Dose (mg/kg ip) | % ILS |
| $N^7$-(4-phosphato-phenl)mitomycin C | 15[a] | 84 |
| | 30[b] | >150 (1/5 30-day survivor) |

45: By Day 6 post-drug

TABLE 5-continued

| | P388 Leukemia Antitumor Activity | |
|---|---|---|
| Drug | Dose (mg/kg ip) | % ILS |
| | injection, body weight for all mice treated with this drug dose decreased by 20-24% | |
| Mitomycin C | 5[c] | 83 |

[a]No weight loss.
[b]Average weight loss = 8%.
[c]Average weight loss = 8%.

Further, in vivo testing will be performed in two parts. Firstly, the host toxicity of the analogues in comparison with the parent drug will be tested. The concentration required to kill approximately 10% of a population of mice will then be determined. Histopathological analysis will determine the effect of drug treatment on tissues and organs. Analysis of white blood cell counts will provide information on hematopoietic toxicity. Preliminary data from one experiment indicates that MC-77 has retained the steep dose response curve for toxicity. 80% and 100% fatalities were observed following one intraperitoneal injection of 30 and 40 mg/kg MC-77 respectively. MC-77 appears to be no more toxic when compared with Mitomycin-C. Currently inconclusive preliminary data suggests that MC-77 may be up to two fold less toxic than the parent drug.

The second stage of in vivo testing will determine antitumor activity. Mice bearing the P388 and MDA-MB-231 tumors will be treated with a range of doses of Mitomycin-C and MC-77. For the ascites tumor P388, increased life span will be utilized as the endpoint. For the solid tumor MDA-MB-231, we will determine the ability of the drugs to inhibit the growth of established tumors and/or to prevent the establishment of tumors from tumor cell inocula. These experiments await the outcome of the toxicity experiments to enable selection of the appropriate drug treatment dosages.

Having now fully described this invention, it will be understood by those of skill in the art that the same can be performed within a wide and equivalent range of conditions, formulations and other parameters without affecting the scope of the invention or any embodiment thereof.

What is claimed is:

1. A mitomycin derivative having the formula:

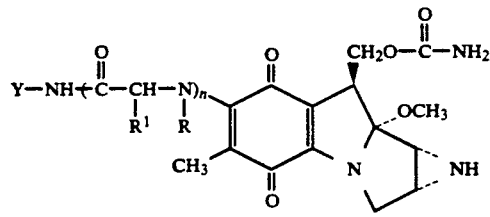

wherein,
n is 0 or 1;
Y is selected from the group consisting of glucopyranosyl, galactopyranosyl, mannopyranosyl, xylopyranosyl, cellobiosyl, lactosyl, glucofuranosyl, maltosyl, and 2-amino-1,3-cyclohexanediol, or the hydroxyl-protected acetate derivatives thereof;
R is hydrogen;
$R^1$ is hydrogen, $C_1$-$C_4$ alkyl or $C_1$-$C_4$ alkyl substituted by phenyl, hydroxyphenyl, indolyl, mercapto, $C_1$-$C_4$ alkylthio, hydroxy, carboxy, amino, guanidino, imidazole or carbamyl; or
R and $R_1$ form a five or six membered ring containing nitrogen.

2. $N^7$-(2-deoxyglucopyranosyl)mitomycin C, a mitomycin derivative of claim 1.
3. $N^7$-(2-deoxygalactopyranosyl)mitomycin C, a mitomycin derivative of claim 1.
4. $N^7$-(tetraacetyl-2-deoxyglucopyranosyl)mitomycin C, a mitomycin derivative of claim 1.
5. $N^7$-(tetraacetyl-2-deoxygalactopyranosyl)mitomycin C, a mitomycin derivative of claim 1.
6. $N^7$-[[[(tetraacetyl-2-deoxy-2-glucopyranosyl)amino]carbonyl]methyl]mitomycin C, a mitomycin derivative of claim 1.
7. $N^7$-[[[(2-deoxyglucopyranosyl)amino]carbonyl]methyl]mitomycin C, a mitomycin derivative of claim 1.
8. A mitomycin derivative having the formula

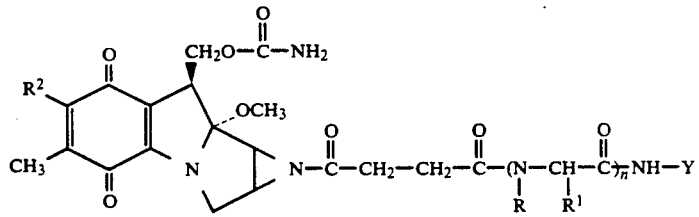

wherein,
n is 0 or 1;
Y is selected from the group consisting of glucopyranosyl, galactopyranosyl, mannopyranosyl, xylopyranosyl, cellobiosyl, lactosyl, glucofuranosyl, maltosyl, and 2-amino-1,3-cyclohexanediol, or the hydroxy-protected acetate derivative thereof;
R is hydrogen;
$R^1$ is hydrogen, $C_1$-$C_4$ alkyl or $C_1$-$C_4$ alkyl substituted by phenyl, hydroxyphenyl, indolyl, mercapto, $C_1$-$C_4$ alkylthio, hydroxy, carboxy, amino, guanidino, imidazole or carbamyl; or
R and $R_1$ form a five or six membered ring containing nitrogen; and
$R^2$ is $NH_2$— or $CH_3O$—.

9. $N^1$-[[2-[[(2-deoxyglucopyranosyl)amino]carbonyl]ethyl]-carbonyl]mitomycin C, a mitomycin derivative of claim 8.
10. $N^1$-[[2-[[(2-deoxyglucopyranosyl)amino]carbonyl]ethyl]carbonyl]mitomycin A, a mitomycin derivative of claim 8.
11. A mitomycin derivative having the formula

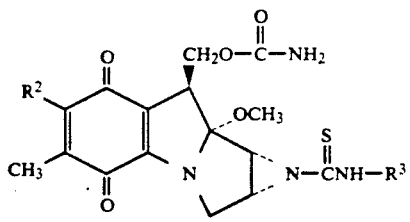

wherein, $R^2$ is $NH_2$— or $CH_3O$—; and $R^3$ is a 3-cyano-4-morpholinyl-2-deoxypyranosyl saccharide or a 4-morpholinyl-2-deoxypyranosyl saccharide.

12. 2-(3-Cyano-4-morpholinyl)-2-deoxyglucopyranosyl-1a-carbothioamide mitomycin, a mitomycin derivative of claim 11.

13. 2-(3-Cyano-4-morpholinyl)-2-deoxygalactopyranosyl-1a-carbothioamide mitomycin, a mitomycin derivative of claim 11.

14. 2-(4-Morpholinyl)-2-deoxyglucopyranosyl-1a-carbothioamide mitomycin, a mitomycin derivative of claim 11.

15. A mitomycin derivative having the formula:

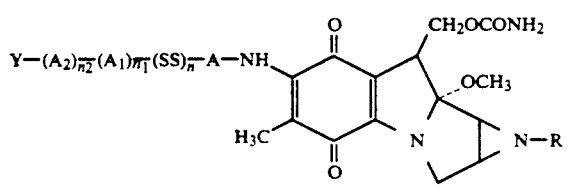

wherein

R is hydrogen, $C_1$-$C_4$ straight or branched alkyl;

A is $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;

n is 0 or 1;

$n_1$ is 0 or 1;

$A_1$ is oxygen, $C_1$-$C_4$ straight or branched saturated or unsaturated alkylene, —C(=O)—NH—, or —NH—C(=O)—;

$A_2$ is oxygen, $C_1$-$C_4$ straight or branched saturated or unsaturated alkylene, NH, NR, or —NH—C(=O)—;

$n_2$ is 0 or 1;

Y is selected from the group consisting of glucopyranosyl, galactopyranosyl, mannopyranosyl, xylopyranosyl, cellobiosyl, lactosyl, glucofuranosyl, maltosyl, and 1,3-cyclohexanediol-2-yl, or a hydroxyl-protected derivative thereof or the corresponding aminosaccharide, diaminosaccharide or triaminosaccharide;

with the proviso that when n is 1, then $A_1$ is a $C_1$-$C_4$ straight or branched saturated or unsaturated alkylene;

with the further proviso that when n is 0, then one of $n_1$ and $n_2$ is 0.

16. 7-{3-[(2-Acetamido-3,4,6-tri-O-acetyl-beta-D-glucopyranosyl)-amino]carbonylpropylamino}-9-methoxymitosane, a mitomycin derivative of claim 15.

17. 7-{2-[(2-Acetamido-3,4,6-tri-O-acetyl-$\beta$-D-glucopyranosyl)amino]carbonylethylamino}-9-methoxymitosane, a mitomycin derivative of claim 15.

18. 7-{[4-(2,3,4,6-Tetra-O-acetyl-$\beta$-D-glucopyranosyl)oxyphenyl]amino}-9-methoxymitosane, a mitomycin derivative of claim 15.

19. 7-{[4-(2,3,4,6-Tetra-O-acetyl-$\beta$-D-glucopyranosyl)dithio]ethylamino}-9-methoxymitosane, a mitomycin derivative of claim 15.

20. 7-{[4-(2-Acetamido-3,4,6-tri-O-acetyl-$\beta$-D-glucopyranosyl)dithio]ethylamino}-9-methoxymitosane, a mitomycin derivative of claim 15.

21. 7-{[4-(2,3,4,6-Tetra-O-acetyl-$\beta$-D-glucopyranosyl)dithio]phenylamino}-9-methoxymitosane, a mitomycin derivative of claim 15.

22. A mitomycin derivative having the formula:

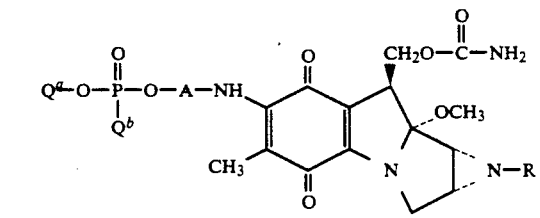

wherein

R is hydrogen, $C_1$-$C_4$ straight or branched alkyl,

A is $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;

$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the formula

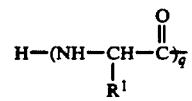

wherein $R^1$ is hydrogen, $C_1$-$C_4$ alkyl, or $C_1$-$C_4$ alkyl substituted by phenyl, hydroxyphenyl, indolyl, mercapto, $C_1$-$C_4$ alkylthio, hydroxy, carboxy, amino, guanidino, imidazolyl or carbamoyl;

q=0–4.

23. $N^7$-(4-phosphatophenyl)mitomycin C, a compound of claim 22.

24. A mitomycin derivative having the formula:

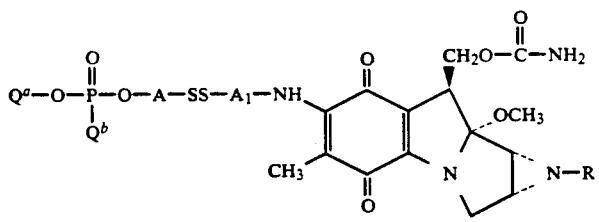

wherein
R is hydrogen, $C_1$-$C_4$ straight or branched alkyl,
A and $A_1$ are $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;
$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the formula

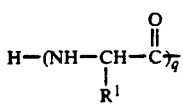

wherein
$R^1$ is hydrogen, $C_1$-$C_4$ alkyl, or $C_1$-$C_4$ alkyl substituted by phenyl, hydroxyphenyl, indolyl, mercapto, $C_1$-$C_4$ alkylthio, hydroxy, carboxy, amino, guanidino, imidazolyl or carbamoyl;
q=0–4.

25. A pharmaceutical composition comprising the mitomycin derivative of any one of claims 1, 8, 11, 15, 22 or 24 and a pharmaceutically acceptable carrier.

26. A method of treating bacterial infection comprising administering to an animal in need of such treatment a pharmaceutical composition comprising an antibacterial amount of the mitomycin derivative of any one of claims 1, 8, 11, 15, 22 or 24 and a pharmaceutically acceptable carrier.

27. The method of claim 26, wherein said bacterial infection is caused by a bacteria selected from the group consisting of Escherichia, Pseudomonas, Salmonella, Staphylococcus, Klebsiella and Listeria.

28. A method for treating cancer by suppressing growth of cancer cells susceptible to growth suppression in an animal comprising administering to an animal in need of such treatment a pharmaceutical composition comprising a cancer cell growth suppressing amount of the mitomycin derivative of any one of claims 1, 8, 11, 15, 22 or 24 and a pharmaceutically acceptable carrier.

29. The method of claim 28, wherein said cancer is selected from the group consisting of leukemia, melanoma, sarcoma, and carcinoma.

30. A process for preparing an $N^7$-substituted mitomycin derivative of the formula:

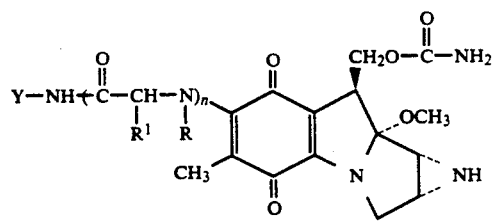

wherein,
n is 0;
Y is selected from the group consisting of glucopyranosyl, galactopyranosyl, mannopyranosyl, xylopyranosyl, cellobiosyl, lactosyl, glucofuranosyl, maltosyl, and 1,3-cyclohexanediol-2-yl, or the hydroxyl-protected derivative thereof;
comprising:
reacting mitomycin A with an amino compound under basic conditions in a polar organic solvent to give the $N^7$-substituted mitomycin.

31. The process of claim 30, wherein said amino compound is selected from the group consisting of glucosamine, galactosamine, mannosamine, xylosamine, cellobiosamine, maltosamine, and 2-amino-1,3-cyclohexanediol.

32. The process of claim 30, wherein said $N^7$-substituted mitomycin is $N^7$-(2-deoxyglucopyranosyl) mitomycin C.

33. A process for preparing a mitomycin derivative having the formula

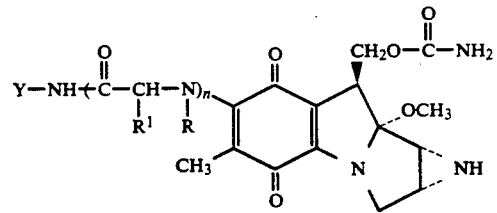

wherein
n is 1;
Y is selected from the group consisting of glucopyranosyl, galactopyranosyl, mannopyranosyl, xylopyranosyl, cellobiosyl, lactosyl, glucofuranosyl, maltosyl, 1,3-cyclohexanediol-2-yl, or the hydroxyl-protected peracetyl derivative thereof;
R is hydrogen;
$R^1$ is hydrogen, $C_1$-$C_4$ alkyl or $C_1$-$C_4$ alkyl substituted by phenyl, hydroxyphenyl, indolyl, mercapto, $C_1$-$C_4$ alkylthio, hydroxy, carboxy, amino, guanidino, imidazole or carbamyl; or
R and $R^1$ together form a five or six membered nitrogen containing ring;

comprising:
(a) condensing an N-protected amino acid with an alcohol in the presence of a dehydration reagent to give an activated ester,
(b) condensing the activated ester obtained in step (a) with an amino compound to give a protected amino acid-amino compound conjugate,
(c) removing the amino acid protecting group of the protected amino acid-amino compound conjugate obtained in step (b) to give an amino acid-amino compound conjugate, and
(d) condensing the amino acid-amino compound conjugate obtained in step (c) with mitomycin A to give the mitomycin derivative.

34. The process of claim 33, wherein said N-protected amino acid is selected from the group consisting of the N-benzyloxycarbonyl derivatives of alanine, valine, leucine, isoleucine, proline, phenylalanine, tryptophan, methionine, glycine, serine, threonine, cysteine, tyrosine, asparagine, glutamine, aspartic acid, glutamine acid, lysine, arginine and histidine.

35. The process of claim 33, wherein the amino acid protecting group is removed by hydrogenolysis.

36. The process of claim 33, wherein the hydroxyl-protected halo derivative is the 1-bromo, 1-Iodo, or 1-chloro derivative of glucopyranose peracetate, glucofuranose peracetate, galactopyranose peracetate, mannopyranose peracetate, xylopyranose peracetate, cellobiose peracetate, lactose peracetate or maltose peracetate.

37. The process of claim 33, wherein the base is a hindered amine selected from diisopropylethylamine, a $C_1$-$C_3$ trialkylamine, DBU or DMAP.

38. A process for the preparation of a mitomycin derivative having the formula:

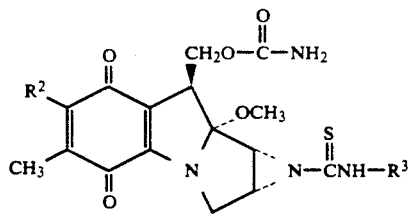

wherein
$R^2$ is $NH_2$— or $CH_3O$—; and
$R^3$ is a 2-(3-cyano-4-morpholinyl)-2-deoxy saccharide;
comprising
(a) condensing bis(acetaldehyde-2-yl) ether with a 2-amino-2-deoxy saccharide in the presence of a salt of cyanoborohydride to give a 2-deoxy-2-(3-cyano-4-morpholinyl) saccharide and a 2-deoxy-4-morpholinyl saccharide;
(b) separation of the 2-deoxy-2-(3-cyano-4-morpholinyl) saccharide from the 2-deoxy-4-morpholinyl saccharide obtained in step (a);
(c) reaction of the 2-deoxy-2-(3-cyano-4-morpholinyl) saccharide obtained in step (b) with an acetyl halide to give a 2-deoxy 1-halo-2-(3-cyano-4-morpholinyl) peracetyl saccharide;
(d) treatment of the 2-deoxy-1-halo-2-(3-cyano-4-morpholinyl) peracetyl saccharide obtained in step (c) with silver thiocyanate to give a saccharide-1-thiocyanate;
(e) reaction of the saccharide-1-thiocyanate obtained in step (d) with mitomycin C or mitomycin A to give a mitomycin C- or mitomycin A-saccharide peracetate carbothioamide; and
(f) hydrolysis of the acetate groups of the mitomycin-C-saccharide peracetate obtained in step (e) to give the mitomycin derivative.

39. A process for the preparation of a mitomycin derivative having the formula:

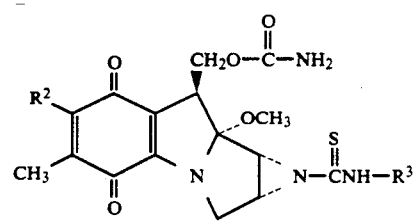

wherein
$R^2$ is $NH_2$— or $CH_3O$—; and
$R^3$ is a (4-morpholinyl)-2-deoxy saccharide;
comprising
(a) condensation of bis(acetaldehyde-2-yl) ether with a 2-amino-2-deoxy saccharide in the presence of a salt of cyanoborohydride to give a 2-deoxy-2-(3-cyano-4-morpholinyl) saccharide and a 2-deoxy-2-(4-morpholinyl) saccharide;
(b) separation of said 2-deoxy-2-(4-morpholinyl) saccharide from said 2-deoxy-2-(3-cyano-4-morpholinyl) saccharide obtained in step (a);
(c) reaction of the 2-deoxy-2-(4-morpholinyl) saccharide obtained in step (b) with an acetyl halide to give a 2-deoxy-1-halo-2-(4-morpholinyl) peracetyl saccharide;
(d) treatment of the 2-deoxy-1-halo-2-(4-morpholinyl) peracetyl saccharide obtained in step (c) with silver thiocyanate to give a saccharide-1-thiocyanate;
(e) reaction of the saccharide-1-thiocyanate obtained in step (d) with mitomycin A or C to give a mitomycin A- or C-saccharide peracetate carbothioamide; and
(f) hydrolysis of the acetate groups of the mitomycin-C-saccharide peracetate obtained in step (e) to give the mitomycin derivative.

40. The process of claim 38 or 39, wherein said 2-amino-2-deoxy saccharide is selected from the group consisting of glucosamine, galactosamine, mannosamine, xylosamine, cellobiosamine and maltosamine.

41. The process of claim 38, wherein said mitomycin derivative is 2-(3-cyano-4-morpholinyl)-2-deoxyglucopyranosylmitomycin-1a-carbothioamide.

42. The process of claim 39, wherein said mitomycin derivative is 2-(4-morpholinyl)-2-deoxyglucopyranosylmitomycin-1a-carbothioamide.

43. A process for the preparation of a mitomycin derivative having the following formula

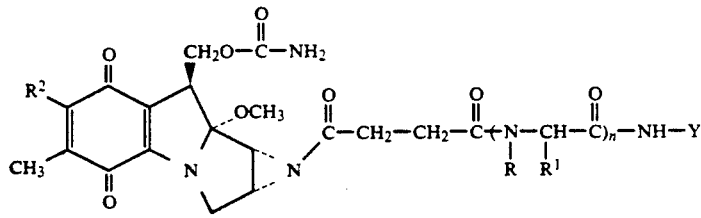

wherein n is 0;

Y is selected from the group consisting of glycopyranosyl, galactopyranosyl, mannopyranosyl, xylopyranosyl, cellobiosyl, lactosyl, glucofuranosyl, maltosyl, 1,3-cyclohexanediol-2-yl;

R is hydrogen;

$R^1$ is hydrogen, $C_1$-$C_4$ alkyl or $C_1$-$C_4$ alkyl substituted by phenyl, hydroxyphenyl, indolyl, mercapto, $C_1$-$C_4$ alkylthio, hydroxy, carboxy, amino, guanidino, imidazole or carbamyl; or R and $R^1$ together form a five or six membered nitrogen containing ring; $R^2$ is $NH_2$— or $CH_3O$—;

comprising:

(a) condensation of mitomycin C with succinic anhydride to give mitomycin C-1a-succinic acid ester;

(b) condensation of the mitomycin C-1a-succinic acid ester obtained in step (a) with a hydroxyl-protected amino derivative selected from the group consisting of glucosamine, galactosamine, mannosamine, xylosamine, cellobiosamine, maltosamine, and 2-amino-1,3-cyclohexanediol; and (c) removal of the hydroxyl protecting groups to give the mitomycin derivative.

44. A process for the preparation of a mitomycin derivative having the following formula

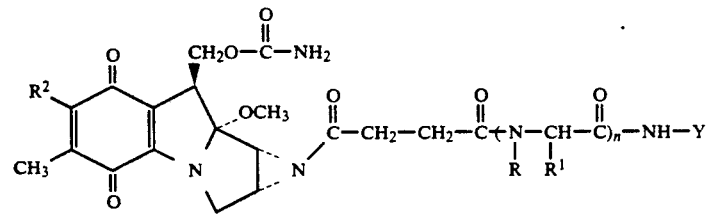

wherein n is 0;

Y is selected from the group consisting of glucopyranosyl, galactopyranosyl, mannopyranosyl, xylopyranosyl, cellobiosyl, lactosyl, glucofuranosyl, maltosyl, 1,3-cyclohexanediol-2-yl;

R is hydrogen;

$R^1$ is hydrogen, $C_1$-$C_4$ alkyl or $C_1$-$C_4$ alkyl substituted by phenyl, hydroxyphenyl, indolyl, mercapto, $C_1$-$C_4$ alkylthio, hydroxy, carboxy, amino, guanidino, imidazole or carbamyl; or R and $R^1$ together form a five or six membered nitrogen containing ring; $R^2$ is $NH_2$— or $CH_3O$—;

comprising:

(a) condensation of mitomycin A with succinic anhydride to give mitomycin A-1a-succinic acid ester;

(b) condensation of the mitomycin A-1a-succinic acid ester obtained in step (a) with a hydroxyl-protected amino acid-saccharide conjugate of the formula

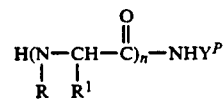

wherein R, $R^1$ and n are as defined above and $Y^P$ is a hydroxyl-protected saccharide selected from the group consisting of the hydroxyl-protected derivatives of glucopyranosyl, galactopyranosyl, mannopyranosyl, xylopyranosyl, cellobiosyl, lactosyl, glucofuranosyl, maltosyl, and 1,3-cyclohexanediol-2-yl; and (c) removal of the hydroxyl protecting groups to give the mitomycin derivative.

45. A process for the preparation of a mitomycin derivative having the formula:

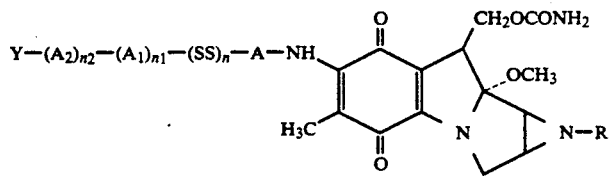

wherein

R is hydrogen, $C_1$-$C_4$ straight or branched alkyl;

A is $C_1$-$C_4$ straight or branched alkylene or unsaturated alkylene, phenylene, substituted phenylene, benzylene (—$CH_2Ph$—), substituted benzylene, heteroaryl, substituted heteroaryl, or $C_3$-$C_6$-heterocycloalkyl;

n is 0;

$n_1$ is 1;

$A_1$ is oxygen;

$n_2$ is 0;

Y is selected from the group consisting of glucopyranosyl, galactopyranosyl, mannopyranosyl, xylopyranosyl, cellobiosyl, lactosyl, and glucofuranosyl, maltosyl, or a hydroxyl-protected derivative thereof or the corresponding aminosaccharide, diaminosaccharide or triaminosaccharide;

comprising:
(a) condensing an acetyl halide with a saccharide (Y—H) to give a 1-halo peracetyl saccharide;
(b) condensing the 1-halo peracetyl saccharide obtained from step (a) with a compound of the formula HO—A—NO$_2$, wherein A is defined as above, to give a nitro saccharide derivative;
(c) reducing the nitro group of the nitro saccharide derivative obtained in step (b) to obtain a primary amino saccharide;
(d) condensing the primary amino saccharide obtained in step (c) with a mitomycin A derivative having the formula:

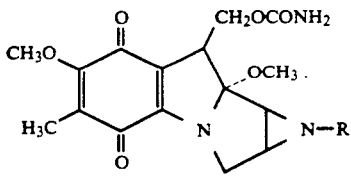

to give a mitomycin-C-saccharide peracetate; and
(e) hydrolysis of the acetate groups of the mitomycin-C-saccharide peracetate obtained in step (d) to give said mitomycin derivative.

46. A process for the preparation of a mitomycin derivative having the formula:

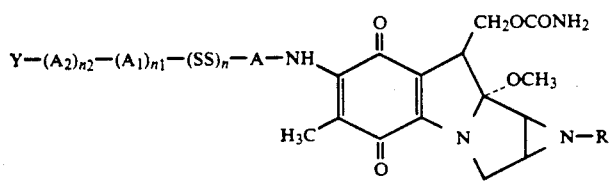

wherein
R is hydrogen, $C_1$-$C_4$ straight or branched alkyl;
A is $C_1$-$C_4$ straight or branched alkylene or unsaturated alkylene, phenylene, substituted phenylene, benzylene (—CH$_2$Ph—), substituted benzylene, heteroaryl, substituted heteroaryl, or $C_3$-$C_6$-heterocycloalkyl;
Y is selected from the group consisting of glucopyranosyl, galactopyranosyl, mannopyranosyl, xylopyranosyl, cellobiosyl, lactosyl, and glucofuranosyl, maltosyl, or a hydroxyl-protected derivative thereof or the corresponding aminosaccharide, diaminosaccharide or triaminosaccharide;
n and $n_1$ are 0;
$n_2$ is 1;
$A_2$ is —NH—C(=O)—; and
comprising:
(a) condensing an acetyl halide with a saccharide to give a 1-halo peracetyl saccharide;
(b) condensing an azide salt with the compound obtained in step (a) to give a 1-azido saccharide derivative;
(c) reducing the 1-azido saccharide derivative obtained in step (b) to obtain a 1-primary amino saccharide;
(d) condensing the 1-primary amino saccharide obtained in step (c) with a compound of the formula PhCH$_2$OC(=O)NH—A— C(=O)OH to give a benzyloxycarbonyl protected saccharide derivative;
(e) reducing the benzyloxycarbonyl protected saccharide derivative formed in step (d) to form a compound of the formula Y—NH—C(=O)—A—NH$_2$;
(f) condensing the compound of the formula Y—NH—C(=O)—A— NH$_2$ obtained in step (e) with a mitomycin A derivative having the formula:

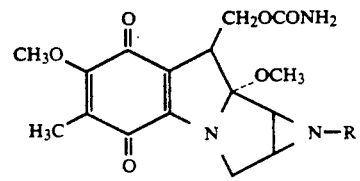

to give a peracetyl saccharide-linked mitomycin derivative; and
(g) hydrolysis of the acetate groups of the peracetyl saccharide-linked mitomycin derivative obtained in step (f) to give said mitomycin derivative.

47. A process for the preparation of a mitomycin derivative having the formula:

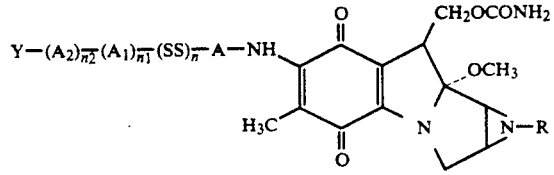

wherein
n is 1;
$n_1$ is 0 or 1;
$n_2$ is 0;
$A_1$ is a $C_1$-$C_4$ straight or branched saturated or unsaturated alkylene;
comprising:
(a) condensing a hydroxy protected compound of the formula Y—(A$_1$)$_{n1}$—SH with a compound of the formula CH$_3$—O— C(=O)—SS—A—NH$_2$ to give Y—(A$_1$)$_{n1}$—SS—A—NH$_2$;
(b) condensing Y—(A$_1$)$_{n1}$—SS—A—NH$_2$ obtained in step (a) with a mitomycin A derivative having the formula:

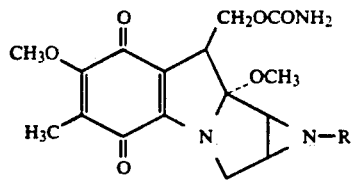

to give a hydroxyl protected saccharide-linked mitomycin derivative; and (c) removal of the protecting groups of the hydroxyl protected saccharide-linked mitomycin derivative obtained in step (b) to give said mitomycin derivative.

48. A process for the preparation of a mitomycin derivative having the formula:

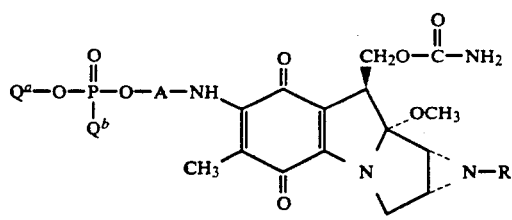

wherein
R is hydrogen, $C_1$–$C_4$ straight or branched alkyl,
A is $C_1$–$C_4$ straight or branched alkylene or unsaturated alkylene, phenylene, substituted phenylene, benzylene (—$CH_2Ph$—), substituted benzylene, heteroaryl, substituted heteroaryl, or $C_3$–$C_6$-heterocycloalkyl;
$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the formula

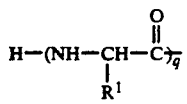

wherein
$R^1$ is hydrogen, $C_1$–$C_4$ alkyl, or $C_1$–$C_4$ alkyl substituted by phenyl, hydroxyphenyl, indolyl, mercapto, $C_1$–$C_4$ alkylthio, hydroxy, carboxy, amino, guanidino, imidazolyl or carbamoyl;
q=0–4;
comprising condensing a compound of formula:

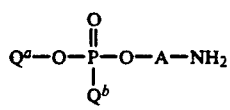

with a mitomycin A derivative of the formula:

49. A process for preparing a mitomycin derivative having the formula:

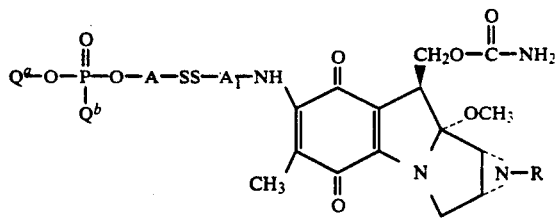

wherein
R is hydrogen, $C_1$–$C_4$ straight or branched alkyl,
A and $A_1$ are $C_1$–$C_4$ straight or branched alkylene or unsaturated alkylene, phenylene, substituted phenylene, benzylene (—$CH_2Ph$—), substituted benzylene, heteroaryl, substituted heteroaryl, or $C_3$–$C_6$-heterocycloalkyl;
$Q^a$ and $Q^b$ are an alkaline metal, glucopyranosyl, galactopyranosyl, mannopyranosyl, xylopyranosyl, cellobiosyl, lactosyl, glucofuranosyl, maltosyl, 1,3-cyclohexanediol-2-yl-, or a protected derivative thereof or the corresponding aminosaccharide, diaminosaccharide or triaminosaccharide, or a group of the formula

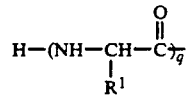

wherein
$R^1$ is hydrogen, $C_1$–$C_4$ alkyl, or $C_1$–$C_4$ alkyl substituted by phenyl, hydroxyphenyl, indolyl, mercapto, $C_1$–$C_4$ alkylthio, hydroxy, carboxy, amino, guanidino, imidazolyl or carbamoyl;
q=0–4;
comprising condensing a compound having the formula:

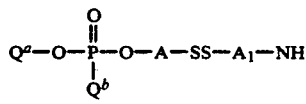

with a mitomycin A derivative having the formula:

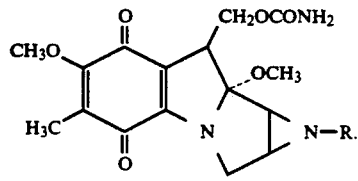

* * * * *